(12) United States Patent
Perner et al.

(10) Patent No.: US 11,642,301 B2
(45) Date of Patent: *May 9, 2023

(54) SYSTEMS, KITS, AND METHODS FOR TREATING HAIR WITH COMPOSITIONS CONTAINING IONIC POLYMERS

(71) Applicant: L'Oreal, Paris (FR)

(72) Inventors: Allison Perner, Metuchen, NJ (US); Jim Singer, South Orange, NJ (US); Siliu Tan, Westfield, NJ (US); Nghi Van Nguyen, Fountain Valley, CA (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/729,441

(22) Filed: Dec. 29, 2019

(65) Prior Publication Data

US 2020/0206121 A1 Jul. 2, 2020

Related U.S. Application Data

(60) Provisional application No. 62/786,595, filed on Dec. 31, 2018.

(51) Int. Cl.
| | | |
|---|---|---|
| *A61K 8/81* | (2006.01) | |
| *A61K 8/34* | (2006.01) | |
| *A61K 8/58* | (2006.01) | |
| *A61K 8/44* | (2006.01) | |
| *A61Q 5/06* | (2006.01) | |
| *A61K 8/41* | (2006.01) | |
| *A61Q 5/12* | (2006.01) | |
| *A61K 8/73* | (2006.01) | |
| *A61K 8/46* | (2006.01) | |
| *A61Q 5/02* | (2006.01) | |

(52) U.S. Cl.
CPC ............ *A61K 8/8147* (2013.01); *A61K 8/342* (2013.01); *A61K 8/416* (2013.01); *A61K 8/44* (2013.01); *A61K 8/463* (2013.01); *A61K 8/585* (2013.01); *A61K 8/73* (2013.01); *A61K 8/8117* (2013.01); *A61K 8/8152* (2013.01); *A61Q 5/02* (2013.01); *A61Q 5/06* (2013.01); *A61Q 5/12* (2013.01); *A61K 2800/5422* (2013.01); *A61K 2800/5424* (2013.01); *A61K 2800/5426* (2013.01); *A61K 2800/5428* (2013.01); *A61K 2800/594* (2013.01); *A61K 2800/596* (2013.01); *A61K 2800/882* (2013.01); *A61K 2800/884* (2013.01)

(58) Field of Classification Search
None
See application file for complete search history.

(56) References Cited

U.S. PATENT DOCUMENTS

| | | | |
|---|---|---|---|
| 3,110,695 A | 11/1963 | Ceresa | |
| 3,304,273 A | 2/1967 | Stamberger | |
| 3,383,351 A | 5/1968 | Stamberger | |
| 3,412,054 A | 11/1968 | Milligan et al. | |
| 3,523,095 A | 8/1970 | Laurito et al. | |
| 5,523,079 A | 6/1996 | Gough | |
| 5,658,558 A | 8/1997 | Schwartz | |
| 9,295,632 B1 | 3/2016 | Benn et al. | |
| 2006/0199742 A1* | 9/2006 | Arisz ..................... A61Q 11/00 507/114 |
| 2007/0197729 A1 | 8/2007 | Wolff et al. | |
| 2009/0136439 A1 | 5/2009 | Feng et al. | |
| 2010/0008885 A1* | 1/2010 | Daly ..................... A61K 8/416 424/70.27 |
| 2011/0120487 A1 | 5/2011 | Rollat-Corvol et al. | |
| 2011/0155163 A1 | 6/2011 | Viravau et al. | |
| 2011/0318286 A1 | 12/2011 | Kawasaki et al. | |
| 2013/0209388 A1* | 8/2013 | Erazo-Majewicz .... A61K 8/731 424/70.13 |
| 2017/0189313 A1* | 7/2017 | Tan .......................... A61K 8/88 |
| 2018/0092826 A1 | 4/2018 | Comeron et al. | |
| 2018/0311139 A1 | 11/2018 | Perner et al. | |

FOREIGN PATENT DOCUMENTS

| | | |
|---|---|---|
| DE | 1152536 B | 8/1963 |
| EP | 0219830 A2 | 4/1987 |
| GB | 1040452 A | 8/1966 |
| WO | 95/23579 A2 | 9/1995 |
| WO | 2015/022259 A1 | 2/2015 |
| WO | 2017/117543 A1 | 7/2017 |

(Continued)

OTHER PUBLICATIONS

Co-Pending U.S. Appl. No. 16/731,013, filed Dec. 30, 2019.
International Preliminary Report on Patentability for counterpart Application No. PCT/US2019/069040, dated Jul. 15, 2021.
Ntematonal Preliminary Report on Patentability for counterpart Application No. PCT/US2019/068978, dated Jul. 15, 2021.
International Search Report and Written Opinion for counterpart Application No. PCT/US2019/069040, dated Mar. 27, 2020.
International Search Report and Written Opinion for counterpart Application No. PCT/US2019/068978, dated Apr. 8, 2020.

(Continued)

Primary Examiner — Dominic Lazaro

(74) Attorney, Agent, or Firm — The Marbury Law Group, PLLC

(57) ABSTRACT

The present disclosure relates to hair care systems comprising: (1) a booster composition containing at least one ionic polymer functionalized with at least one carboxylic acid moiety; optionally, at least one compound selected from an alkoxysilane, a nonionic latex polymer, or mixtures thereof; a thickening agent; and a cosmetically acceptable carrier; and (2) a hair treatment composition containing at least one surfactant selected from an anionic surfactant, an amphoteric surfactant, a cationic surfactant, a nonionic surfactant, or mixtures thereof. The hair care systems of the present disclosure can be used to clean and/or condition hair, as well impart frizz control and manageability benefits to hair.

18 Claims, No Drawings

(56) References Cited

FOREIGN PATENT DOCUMENTS

WO 2017/165931 A1 10/2017
WO 2018/218009 A2 11/2018

OTHER PUBLICATIONS

Mintel: "Discovery Kit Smoothing," Sisley, XP055681229, Aug. 10, 2018.
Mintel: "Hair on the Go Kit," Jonathan Product, XP055681416, Oct. 17, 2008.
Non-Final Office Action for copending U.S. Appl. No. 16/731,013, dated Nov. 6, 2020.
Woodruff, Hair Care Feature, Published in SPC 2011, http://creative-developments.co.uk/wp-concent/uploads/2013/10/Hair-Care-2011.pdf (Year: 2011).
Final Office Action for copending U.S. Appl. No. 16/731,013, dated Jun. 14, 2021.
Non-Final Office Action for copending U.S. Appl. No. 16/731,013, dated Mar. 15, 2022.
Final Office Action for copending U.S. Appl. No. 16/731,013, dated Aug. 23, 2022.

* cited by examiner

SYSTEMS, KITS, AND METHODS FOR TREATING HAIR WITH COMPOSITIONS CONTAINING IONIC POLYMERS

This application claims priority to U.S. Provisional Patent Application No. 62/786,595, filed Dec. 31, 2018.

TECHNICAL FIELD

The instant disclosure relates to systems, kits, compositions, and methods for treating hair, such as for cleansing and conditioning hair, as well as for imparting improved frizz control and hair manageability properties to hair.

BACKGROUND

Individuals desire healthy and strong hair, as healthy looking hair is in general a sign of good health and good hair-care practices. Nonetheless, nutrition, environmental influences, and chemical hair treatments can lead to hair damage that significantly weakens and dulls the hair over time. Gloss and moisture balance are deleteriously affected, making the hair more difficult to comb and style. Furthermore, dry hair that has been weakened or damages is also prone to be frizzy, to have breakage, and to the formation of "split ends."

Nutrition plays a crucial role in the health of hair, but nutrition alone is not sufficient to compensate for the various types of physical, chemical, and environmental damage that prevent optimal hair quality. Physical hair damage is often the result of repeatedly manipulating the shape of the hair. For example, hair styles such as ponytails, buns, and braiding are quick and easy but when done too often and too tightly, can impart strain on the edges of the hair and cause a receding hair line. Hair also becomes physically damaged during detangling and styling. Excessive detangling can result in split ends and breakage.

The environment also influences the health of hair. Regions with hard water can affect the look, feel, and shine of the hair. This is because hard water leaves mineral deposits, which accumulate over time on the hair and eventually prevents moisture intake into the hair. The hair becomes dry, frizzy, and is prone to tangles. Environmental factors, such as strong sun, wind, cold air, extreme temperature variations, and changes in air humidity can also damage the hair. The static and dry winter air contributes to moisture loss. Abrupt change from cold outdoor air to warm indoor air can cause the cuticle layers of the hair to lose moisture quickly into the atmosphere. Environmental effects on the hair, however, cannot be completely avoided. Thus, mechanisms to reduce or prevent damage to hair, and products that can nourish and re-condition hair are useful for improving the quality of hair.

One other factor that can lead to making the hair feel more damaged, tangled, more dry, and less soft/smooth is the cleansing process that involves the use of shampoos. Shampoos contain detergents or surfactants such as anionic surfactants which, while they produce good foams and effectively cleanse the hair, can also contribute to these adverse effects on hair.

The development of cleansing compositions has been driven by a need for certain performance properties and textures that consumers find desirable. Not only do consumers seek cleansing compositions that foam and cleanse well, consumers also desire to use products that are mild to the hair, do not damage or tangle the hair, and have sufficient "thickness" (viscosity) that do not easily drip and yet are easy to dispense, apply, and spread on the hair. The cleansing compositions should also rinse away from the body with ease. Thus, in addition to selecting the appropriate type of anionic surfactants, other ingredients may be needed in order to provide a desirable viscosity and texture to cleansing and personal care products.

In order to further improve the integrity, look, and feel of hair, including hair that has become dry or damaged or tangled either as a result of environmental or chemical factors and/or cleansing processes, consumers turn to hair conditioners that leave the hair feeling soft, supple and conditioned.

Hair conditioners are products that are applied to hair to alter the hair's texture, appearance, shine, etc. Hair conditioners are often viscous liquids that are applied and massaged into the hair typically after the hair has been washed with a shampoo. Conditioners can hydrate, soften, and help to detangle hair. Cationic surfactants (compounds that have a cationic counterion or compounds that can be cationically charged depending on the pH of a composition) can be added into conditioners in order to enhance the conditioning properties of such products, but cationic surfactants are generally easily washed off from the hair, especially upon a consecutive shampooing step. One solution is to include silicones into conditioners because they can provide additional smoothing benefits to hair and contribute to the wash resistance of the conditioners. However, silicone compounds can also weigh the hair down too much and make it more difficult to style the hair after the shampooing-conditioning process. Thus, not only do manufacturers of hair care products continue to seek the right balance of the amount and/or types of ingredients or combinations of ingredients, manufacturers also continue to develop alternative methods of providing hair care benefits to the hair during and after the cleansing process.

BRIEF SUMMARY

The present disclosure relates to hair care systems, kits, and methods for cleansing and conditioning hair which employ compositions that include one or more surfactants and a combination of one or more ionic polymers with an alkoxysilane and/or a nonionic polymer, in particular, a nonionic latex polymer. A unique feature of the systems and methods of the present disclosure is that they can utilize various types of hair care compositions, such as shampoos and conditioners (both rinse-off compositions), or as rinse-off or leave-in masks (masques) or pre-shampoo treatments. In addition to the cleansing and conditioning benefits that are typically provided to hair, the systems, methods, and compositions of the present disclosure provide one or more additional benefits such as frizz control, detangling, combability, hair manageability, and/or styling and/or shaping of the hair.

The hair care systems include (1) booster compositions containing synergistic combinations of at least one ionic polymer and optionally at least one alkoxysilane and/or at least one nonionic latex polymer, and (2) surfactant-containing hair treatment compositions, such as shampoos, conditioners, masques, and pre-shampoo treatments. The ionic polymer can be selected from bimodal agents, amphoteric polymers, anionic polymers, cationic polymers, or mixtures thereof.

When the hair treatment compositions and the booster compositions are combined and applied onto hair, the compositions were found to impart one or more properties of improved frizz control of hair, manageability of hair, no buildup of product, ease of distribution, detangling, suppleness, and smoothness of hair, and ease of styling and/or shaping hair, in addition to the typical benefits of good foaming and lather and/or conditioning provided by traditional shampoos, conditioners, or masques. Thus, the hair care system of the instant disclosure typically includes at least the following combination of components:

(1) a booster composition comprising:
  (a) at least one ionic polymer functionalized with at least one carboxylic acid moiety;
  (b) optionally, at least one compound selected from:
    (i) at least one alkoxysilane;
    (ii) at least one nonionic latex polymer; and
    (iii) a mixture thereof;
  (c) at least one thickening agent; and
  (d) a cosmetically acceptable carrier;
(2) at least one hair treatment composition comprising at least one surfactant selected from anionic surfactants, amphoteric surfactants, cationic surfactants, nonionic surfactants, or mixtures thereof.

The at least one ionic polymer includes at least one unsaturated alkylene-containing-carboxylic acid-based monomer and can be selected from bimodal agents, amphoteric (non-latex) polymers, anionic polymers, cationic polymers, or mixtures thereof.

The at least one ionic polymer functionalized with at least one carboxylic acid moiety includes at least one (poly)carboxylic acid compound and can include at least one (meth)acrylic acid-based and/or at least one (meth)acrylate-based monomer.

The at least one bimodal agent comprises a polymeric component having at least one anionic functionality and a polymeric component having at least one cationic functionality and includes latex polymers that can also be called amphoteric latex polymers.

The at least one anionic polymer can be selected from anionic latex polymers and anionic non-latex polymers.

The at least one cationic polymer can be selected from cationic latex polymers and cationic non-latex polymers.

The at least one alkoxysilane is preferably a silane with least one solubilizing functional group such as an ethoxy group and at least one amino substituent.

The at least one nonionic latex polymer preferably has at least one (meth)acrylate-based monomer.

The hair treatment compositions of the instant disclosure may, for example, be in the form of a shampoo, a conditioner, a rinse-out masque, a leave-in treatment product, or a pre-shampoo treatment product.

The instant disclosure is also directed to methods for treating and/or cleansing and/or conditioning and/or styling/shaping hair with a hair care system, and to methods for imparting frizz control to hair with a hair care system, the methods comprising the steps of:

(A) combining, in order to form a mixture (i.e., the hair care system):
  (1) a booster composition comprising:
    (a) at least one ionic polymer functionalized with at least one carboxylic acid moiety;
    (b) optionally, at least one compound selected from:
      (i) at least one alkoxysilane;
      (ii) at least one nonionic latex polymer; and
      (iii) a mixture thereof;
    (c) at least one thickening agent; and
    (d) a cosmetically acceptable carrier;
  (2) at least one hair treatment composition comprising at least one surfactant selected from anionic surfactants, amphoteric surfactants, cationic surfactants, nonionic surfactants, or a mixture thereof;
(B) contacting the hair with the mixture/hair care system; and
(C) optionally, rinsing the mixture from the hair.

According to numerous variations of the disclosure, one or more hair treatment compositions (2) containing the at least one surfactant, such as a shampoo, a conditioner, a masque, a pre-shampoo treatment, or a leave-in treatment, can be individually combined with a booster composition (1) according to the disclosure, in order to form various hair care mixtures or systems that may be applied to hair to treat the hair, and to provide improved properties such as frizz control and manageability. Thus, various combinations of hair treatment compositions and booster compositions according to the disclosure, as well as routines or methods of treating hair, are contemplated. By way of non-limiting example, a hair treatment composition according to the disclosure in the form of a shampoo containing at least one anionic surfactant can be combined with a booster composition according to the disclosure, and the resulting mixture can be used to cleanse the hair. According to further embodiments, the cleansed hair may then optionally be conditioned, either with a traditional conditioner or with a hair treatment composition according to the disclosure in the form of a conditioner that has been combined with a booster composition according to the disclosure. Optionally, hair that has been shampooed and/or conditioned according to various embodiments of the disclosure may be treated with a rinse-out masque composition or with a leave-in hair treatment composition that has been combined with a booster composition according to the disclosure.

Finally, the instant disclosure relates to kits comprising the hair treatment compositions and booster compositions. Such kits may include (1) one or more booster compositions as described above, and (2) one or more hair treatment compositions, such as in the form of a shampoo, a conditioner, a masque, a leave-in treatment product, or a pre-shampoo treatment product, wherein the hair treatment compositions or products and booster compositions are separately contained such that they may be included in separate bottles or containers, or may be included in an assembly or unitary device or packaging that separately houses the hair treatment composition or product and booster composition. Instructions, mixing components, brushes, gloves, measuring tools, etc., may also be included in the kits.

DESCRIPTION

The hair care systems of the instant disclosure typically include:

(1) a booster composition comprising:
  (a) at least one ionic polymer functionalized with at least one carboxylic acid moiety;
  (b) optionally, at least one compound selected from:
    (i) at least one alkoxysilane;
    (ii) at least one nonionic latex polymer; and
    (iii) a mixture thereof;
  (c) at least one thickening agent; and
  (d) a cosmetically acceptable carrier;
(2) at least one hair treatment composition comprising at least one surfactant selected from anionic surfactants, amphoteric surfactants, cationic surfactants, nonionic surfactants, or a mixture thereof.

In an embodiment, the at least one ionic polymer functionalized with at least one carboxylic acid moiety is present in an amount of about 0.1 to about 10 wt %, or from about 0.15 to about 8 wt %, or from about 0.2 to about 5 wt %, or from about 0.3 to about 4 wt %, of the booster composition, including ranges and sub-ranges therebetween.

In an embodiment, the at least one ionic polymer functionalized with at least one carboxylic acid moiety is present in an amount of about 0.1 to about 10 wt %, or from about 0.15 to about 8 wt %, or from about 0.2 to about 5 wt %, or from about 0.3 to about 4 wt %, of the booster composition, including all ranges and sub-ranges therebetween.

In an embodiment, the at least one ionic polymer includes at least one unsaturated alkylene-containing-carboxylic acid-based monomer.

In an embodiment, the at least one ionic polymer includes at least one (meth)acrylic acid-based and/or at least one (meth)acrylate-based monomer.

In an embodiment, the at least one ionic polymer includes at least one (poly)carboxylic acid compound having at least one (meth)acrylic acid-based and/or at least one (meth)acrylate-based monomer.

In an embodiment, the at least one ionic polymer functionalized with at least one carboxylic acid moiety is selected from at least one bimodal agent(s), at least one amphoteric polymer, at least one anionic polymer, at least one cationic polymer, or mixtures thereof.

In an embodiment, the at least one ionic polymer functionalized with at least one carboxylic acid moiety is selected from at least one bimodal agent.

In an embodiment, the at least one bimodal agent comprises a polymeric component having at least one anionic functionality and a polymeric component having at least one cationic functionality.

In an embodiment, the at least one bimodal agent may be chosen from latex polymers.

In an embodiment, the at least one bimodal agent is selected from polyquaternium-91 (and) polyacrylate-15, polyacrylate-21 (and) acrylates/dimethylaminoethyl methacrylate copolymer, acrylates/ethylhexyl acrylate/hema copolymer (and) acrylates/diethylaminoethyl methacrylate/ethylhexyl acrylate copolymer, polyacrylate-15 (and) polyacrylate-17, polyacrylate-18 (and) polyacrylate-19, polyacrylate-16, or mixtures thereof.

In an embodiment, the at least one ionic polymer functionalized with at least one carboxylic acid moiety is selected from least one amphoteric polymer.

In an embodiment, the at least one amphoteric polymer is selected from polyquaternium-22, polyquaternium-39, polyquaternium-47, polyquaternium-53, polyquaternium-61, polyquaternium-69, polyquaternium-86, polyquaternium-95, or mixtures thereof.

In an embodiment, the at least one ionic polymer functionalized with at least one carboxylic acid moiety is selected from at least one anionic polymer that is an anionic latex polymer or an anionic non-latex polymer.

In an embodiment, the at least one anionic polymer includes at least one anionic latex polymer selected from Polyacrylate-15, Polyacrylate-21, Polyacrylate-17, Polyacrylate-18, Polyacrylate-19, a branched anionic acrylate copolymer Polyacrylate-2 Crosspolymer, Acrylates Crosspolymer-3, Polyacrylate-14, and those sold under the SYNTRAN series as commercially available from Interpolymer such as Acrylates Copolymer, Styrene/Acrylates/Ammonium Methacrylate Copolymer and Ammonium Acrylates Copolymer and polyurethane-1, polyurethane-34, polyurethane-14/AMP-acrylates copolymer blend, acrylates copolymers of two or more monomers of (meth)acrylic acid or one of their simple esters, or mixtures thereof.

In an embodiment, the at least one anionic polymer includes at least one anionic non-latex polymer selected from copolymers of acrylic acid or acrylic esters.

In an embodiment, the anionic non-latex polymers are selected from Polyacrylate-15, Polyacrylate-21, Polyacrylate-17, Polyacrylate-18, Polyacrylate-19, acrylic acid/ethyl acrylate/N-tert-butylacrylamide terpolymers, copolymers derived from crotonic acid, such as the vinyl acetate/vinyl tert-butylbenzoate/crotonic acid terpolymers and the crotonic acid/vinyl acetate/vinyl neododecanoate terpolymers, polymers derived from maleic, fumaric or itaconic acids or anhydrides with vinyl esters, vinyl ethers, vinyl halides, phenylvinyl derivatives, or acrylic acid and its esters, such as the methyl vinyl ether/monoesterified maleic anhydride copolymers, the copolymers of methacrylic acid and of methyl methacrylate, the copolymers of methacrylic acid and of ethyl acrylate, the vinyl acetate/crotonic acid copolymers and the vinyl acetate/crotonic acid copolymers grafted by polyethylene glycol, those anionic polymers as sold under the FIXATE series as commercially available from Lubrizol, such as a branched block anionic polymer sold as FIXATE G-100, those sold under the CARBOPOL series as commercially available from Lubrizol such as Acrylates Crosspolymer-4 (CARBOPOL AQUA SF-2), Acrylates Crosspolymer-4 (CARBOPOL AQUA CC), Acrylates Copolymer (CARBOPOL AQUA SF-1) carbomers, acrylates/C10-30 alkyl acrylates crosspolymers, the polymer known under the INCI name Acrylates/Steareth-20 Methacrylate Crosspolymer, Acrylates/Palmeth-25 Acrylate Copolymer, Acrylates/Palmeth-20 Acrylate Copolymer, or mixtures thereof.

In an embodiment, the anionic non-latex polymer(s) may preferably be selected from Polyacrylate-15, Polyacrylate-21, Polyacrylate-17, Polyacrylate-18, Polyacrylate-19, octylacrylamide/acrylates/butylamino ethyl (meth)acrylate copolymer, acrylic acid/C10-C30 alkyl acrylate crosslinked copolymers, crotonic acid/vinyl acetate/vinyl neododecanoate terpolymers, acrylates copolymer, polyacrylate-2, polyacrylate-21, or mixtures thereof.

In an embodiment, the at least one ionic polymer functionalized with at least one carboxylic acid moiety is selected from at least one cationic polymer. In an embodiment, the at least one cationic polymer includes at least one cationic latex polymer.

In an embodiment, the at least one cationic polymer is selected from Polyquaternium-91, Polyquaternium-4, Polyquaternium-11, Polyquaternium-16, Polyquaternium-68, or mixtures thereof.

In various exemplary embodiments, the composition comprises a neutralizing agent. In at least certain embodiments, the neutralizing agent may be selected from the group consisting of: potassium hydroxide, sodium hydroxide, triisopropanolamine (TIPA), 2-aminobutanol, 2-aminomethyl propanol (AMP), aminoethylpropandiol, dimethyl stearamine (Armeen 18 D), sodium silicate, tetrahydroxypropyl ethylenediamine (Neutrol® TE), ammonia (NH3), triethanolamine, trimethylamine (Tris Amino Ultra), aminomethylpropandiol (AMPD) or mixtures thereof. The neutralizing agent may be 2-aminomethyl propanol.

In an embodiment, the neutralizing agent is employed to neutralize the at least one ionic polymer of the present disclosure.

In an embodiment, the at least one ionic polymer may be present in neutralized or partially neutralized form.

In an embodiment, the at least one compound (b) is selected from at least one alkoxysilane or at least one nonionic latex polymer and is present in an amount of from about 0.05 to about 10 wt %, or from about 0.1 to about 8 wt %, or from about 0.15 to about 6 wt %, or from about 0.2 to about 5 wt %, of the booster composition, including ranges and sub-ranges therebetween.

In an embodiment, the at least one compound (b) is selected from at least one alkoxysilane and is present in an amount of from about 0.05 to about 5 wt %, or from about 0.1 to about 4 wt %, or from about 0.15 to about 3 wt %, or from about 0.2 to about 2.5 wt %, of the booster composition, including ranges and sub-ranges therebetween.

In an embodiment, the at least one alkoxysilane has at least one solubilizing functional group and at least one amino substituent.

In an embodiment, the at least one alkoxysilane has at least one solubilizing functional group and at least one amino substituent and is a compound of formula (I):

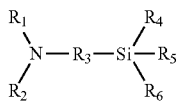

(I)

wherein:
$R_4$ is chosen from halogens, OR', and R'$_1$;
$R_5$ is chosen from halogens, OR", and R'2;
$R_6$ is chosen from halogens, OR''', and R'3; and
$R_1$, $R_2$, $R_3$, R', R", R''', R'$_1$, R'$_2$, and R'$_3$, which may be identical or different, are independently chosen from linear and branched, saturated and unsaturated hydrocarbon-based groups optionally bearing additional chemical groups such as acid or amine groups, it also being possible for $R_1$, $R_2$, R', R", and R''' to be hydrogens, and at least two of the $R_4$, $R_5$, and $R_6$ groups are different from the R'$_1$, R'$_2$, and R'3 groups.

In an embodiment, the at least one alkoxysilane has at least one solubilizing functional group and at least one amino substituent and is a compound of formula (Ia):

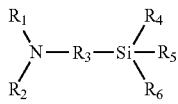

(Ia)

wherein:
$R_4$ is chosen from OR' groups;
$R_5$ is chosen from OR" groups;
$R_6$ is chosen from OR''' groups;
$R_1$ and $R_2$ are chosen from hydrogen; and
$R_3$, R', R", R''', which may be identical or different, are independently chosen from linear and branched, saturated and unsaturated hydrocarbon groups, optionally bearing at least one additional chemical group, wherein R', R", and R''' may also be chosen from hydrogen.

In an embodiment, the alkoxysilane comprises 3-aminopropyltriethoxysilane.

In an embodiment, the at least one compound (b) is selected from at least one nonionic latex polymer and is present in an amount of from about 0.05 to about 5 wt %, or from about 0.1 to about 4 wt %, or from about 0.15 to about 3 wt %, or from about 0.2 to about 2.5 wt %, of the booster composition, including ranges and sub-ranges therebetween.

In an embodiment, the at least one nonionic latex polymer is selected from acrylates copolymer (DAITOSOL 5000 AD, Kobo Products, Inc.), polyacrylate-2 crosspolymer (DAITOSOL 5000 SJ, Kobo Products, Inc.), styrene/acrylates copolymer (DAITOSOL 5000 STY, Kobo Products, Inc.), acrylates/ethylhexyl acrylate copolymer (DAITOSOL 4000 SJT, Kobo Products, Inc.), or mixtures thereof.

In an embodiment, the at least one surfactant includes at least one anionic surfactant selected from alkyl sulfates, alkyl ether sulfates, acyl isethionates, acyl sarcosinates, alkyl sulfonates, alkyl sulfosuccinates, alkyl sulfoacetates, acyl amino acid surfactants other than acyl sarcosinates and selected from acyl taurates, acyl glycinates, acyl glutamates, alkoxylated monoacids, salts thereof, or mixtures thereof.

In an embodiment, the at least one surfactant includes at least one amphoteric surfactant selected from betaines, alkyl amphoacetates, alkyl amphoprionates, salts thereof, or mixtures thereof.

In an embodiment, the betaines are selected from alkyl betaines, alkyl amidopropyl betaines, alkyl sulfobetaines (sultaines), or mixtures thereof.

In an embodiment, the amphoteric surfactants are selected from cocamidopropyl betaine, coco-betaine, or mixtures thereof.

In an embodiment, the at least one surfactant includes at least one cationic surfactant selected from a quaternary ammonium compound that is a mono- or double-chain quaternary ammonium compound, wherein each chain independently has from about 14 to about 30 carbon atoms; and the quaternary ammonium compound has a cosmetically acceptable counterion selected from chloride, bromide, and methosulfate.

In an embodiment, the at least one surfactant includes at least one cationic surfactant selected from cetrimonium chloride, cetrimonium methosulfate, stearimonium chloride, behentrimonium chloride, behentrimonium methosulfate, behenamidopropyltrimonium methosulfate, stearamidopropyltrimonium chloride, arachidtrimonium chloride, distearyldimonium chloride, cetyltrimethylammonium chloride, cetyltrimethylammonium bromide, dipalmitoylethyl hydroxyethylmonium methosulfate, dicetyldimonium chloride (Varisoft 432 PPG), tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamido-propyldiethylamine, behenamidoethyldiethylamine, behenamidoethyldimethylamine, arachidamidopropyldimethylamine, arachidamidopropyldiethylamine, arachidam ido-ethyldiethylamine, arachidamidoethyldimethylamine, brassicam idopropyldimethyl-amine, or mixtures thereof.

In an embodiment, the at least one surfactant includes at least one nonionic surfactant selected from alkyl polyglucosides, fatty alcohols, alkoxylated fatty alcohols, sorbitan derivatives, glyceryl esters, or mixtures thereof.

In an embodiment, the hair treatment and/or booster compositions of the instant disclosure comprise at least one fatty compound.

In an embodiment, the at least one fatty compound is selected from the group consisting oils, mineral oil, alkanes, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, ceramide, or mixtures thereof.

In an embodiment, the hair treatment and/or booster compositions of the instant disclosure comprise at least one silicone.

In an embodiment, the booster compositions of the instant disclosure comprise at least one thickener selected from polysaccharides, gums, starches, clays, or mixtures thereof.

In an exemplary embodiment, the booster compositions of the instant disclosure comprise: (a) at least one ionic polymer functionalized with at least one carboxylic acid moiety selected from at least one bimodal agent, at least one amphoteric polymer, at least one anionic polymer, at least one cationic polymer, or mixtures thereof; and (b) at least one compound selected from (b)(i) at least one alkoxysilane of formula (I). In a further exemplary embodiment, the composition also comprises (b)(ii) at least one nonionic latex polymer selected from acrylates copolymer (DAITOSOL 5000 AD, Kobo Products, Inc.), polyacrylate-2 crosspolymer (DAITOSOL 5000 SJ, Kobo Products, Inc.), styrene/acrylates copolymer (DAITOSOL 5000 STY, Kobo Products, Inc.), acrylates/ethylhexyl acrylate copolymer (DAITOSOL 4000 SJT, Kobo Products, Inc.), or mixtures thereof.

In an exemplary embodiment, the booster compositions of the instant disclosure comprise: (a) at least one ionic polymer functionalized with at least one carboxylic acid moiety selected from at least one bimodal agent, at least one amphoteric polymer, at least one anionic polymer, at least one cationic polymer or mixtures thereof; and (b) at least one compound selected from (b)(ii) at least one nonionic latex polymer selected from acrylates copolymer (DAITOSOL 5000 AD, Kobo Products, Inc.), polyacrylate-2 crosspolymer (DAITOSOL 5000 SJ, Kobo Products, Inc.), styrene/acrylates copolymer (DAITOSOL 5000 STY, Kobo Products, Inc.), acrylates/ethylhexyl acrylate copolymer (DAITOSOL 4000 SJT, Kobo Products, Inc.).

In an exemplary embodiment, the booster compositions of the instant disclosure comprise: (a) at least one ionic polymer functionalized with at least one carboxylic acid moiety selected from at least one bimodal agent(s) comprising a polymeric component having at least one anionic functionality and a polymeric component having at least one cationic functionality, and wherein the at least one bimodal agent includes latex polymer(s); and (b) a least one compound selected from: (b)(i) at least one alkoxysilane of formula (I); (b)(ii) at least one nonionic latex polymer selected from acrylates copolymer (DAITOSOL 5000 AD, Kobo Products, Inc.), polyacrylate-2 crosspolymer (DAITOSOL 5000 SJ, Kobo Products, Inc.), styrene/acrylates copolymer (DAITOSOL 5000 STY, Kobo Products, Inc.), acrylates/ethylhexyl acrylate copolymer (DAITOSOL 4000 SJT, Kobo Products, Inc.), or mixtures thereof; or (b)(iii) a mixture of (b)(i) and (b)(ii).

In an embodiment, the at least one bimodal agent(s) is selected from polyquaternium-91 (and) polyacrylate-15, polyacrylate-21 (and) acrylates/dimethylaminoethyl methacrylate copolymer (marketed under the name Syntran PC 5100 by Interpolymer), acrylates/ethylhexyl acrylate/hema copolymer (and) acrylates/diethylaminoethyl methacrylate/ethylhexyl acrylate copolymer (marketed under the name Syntran PC 5775 by Interpolymer), polyacrylate-15 (and) polyacrylate-17 (marketed under the name Syntran PC 5227 by Interpolymer), polyacrylate-18 (and) polyacrylate-19 (marketed under the name Syntran PC 5107 by Interpolymer), polyacrylate-18 (and) polyacrylate-19 (marketed under the name Syntran PC 5117 by Interpolymer), polyacrylate-16 (Syntran PC 5112), or mixtures thereof.

In an exemplary embodiment, the booster compositions of the instant disclosure comprise: (a) at least one ionic polymer functionalized with at least one carboxylic acid moiety selected from amphoteric polymers selected from polyquaternium-22, polyquaternium-39, polyquaternium-47, polyquaternium-53, polyquaternium-61, polyquaternium-69, polyquaternium-86, polyquaternium-95, or mixtures thereof; and (b) a least one compound selected from: (b)(i) at least one alkoxysilane of formula (I); (b)(ii) at least one nonionic latex polymer selected from acrylates copolymer (DAITOSOL 5000 AD, Kobo Products, Inc.), polyacrylate-2 crosspolymer (DAITOSOL 5000 SJ, Kobo Products, Inc.), styrene/acrylates copolymer (DAITOSOL 5000 STY, Kobo Products, Inc.), acrylates/ethylhexyl acrylate copolymer (DAITOSOL 4000 SJT, Kobo Products, Inc.); or (b)(iii) a mixture of (b)(i) and (b)(ii).

In an embodiment, the booster compositions of the instant disclosure comprise: (a) at least one ionic polymer functionalized with at least one carboxylic acid moiety selected from anionic polymers; and (b) a least one compound selected from: (b)(i) at least one alkoxysilane of formula (I); (b)(ii) at least one nonionic latex polymer selected from acrylates copolymer (DAITOSOL 5000 AD, Kobo Products, Inc.), polyacrylate-2 crosspolymer (DAITOSOL 5000 SJ, Kobo Products, Inc.), styrene/acrylates copolymer (DAITOSOL 5000 STY, Kobo Products, Inc.), acrylates/ethylhexyl acrylate copolymer (DAITOSOL 4000 SJT, Kobo Products, Inc.), or mixtures thereof; or (b)(iii) a mixture of (b)(i) and (b)(ii).

In an exemplary embodiment, the anionic polymers are selected from Polyacrylate-15, Polyacrylate-21, Polyacrylate-17, Polyacrylate-18, Polyacrylate-19, the acrylic acid/ethyl acrylate/N-tert-butylacrylamide terpolymers sold in particular under the name ULTRAHOLD STRONG by BASF, copolymers derived from crotonic acid, such as the vinyl acetate/vinyl tert-butylbenzoate/crotonic acid terpolymers and the crotonic acid/vinyl acetate/vinyl neododecanoate terpolymers sold in particular under the name RESIN 28-29-30 by National Starch, polymers derived from maleic, fumaric or itaconic acids or anhydrides with vinyl esters, vinyl ethers, vinyl halides, phenylvinyl derivatives, or acrylic acid and its esters, such as the methyl vinyl ether/monoesterified maleic anhydride copolymers sold, for example, under the name GANTREZ by ISP, the copolymers of methacrylic acid and of methyl methacrylate sold under the name EUDRAGIT L by Rohm Pharma, the copolymers of methacrylic acid and of ethyl acrylate sold under the name LUVIMER MAEX or MAE by BASF, the vinyl acetate/crotonic acid copolymers sold under the name LUVISET CA 66 by BASF and the vinyl acetate/crotonic acid copolymers grafted by polyethylene glycol sold under the name ARISTOFLEX A by BASF, those anionic polymers as sold under the FIXATE series as commercially available from Lubrizol, such as a branched block anionic polymer sold as FIXATE G-100, those sold under the CARBOPOL series as commercially available from Lubrizol such as Acrylates Crosspolymer-4 (CARBOPOL AQUA SF-2), Acrylates Crosspolymer-4 (CARBOPOL AQUA CC), Acrylates Copolymer (CARBOPOL AQUA SF-1), carbomers (trade names CARBOPOL 980, CARBOPOL 981, CARBOPOL 5984, CARBOPOL ETD 2050 and CARBOPOL Ultrez-10 Polymer, all from the Lubrizol Company), acrylates/C10-30 alkyl acrylates crosspolymers (trade names CARBOPOL 1382, CARBOPOL ETD 2020, PEMULEN TR-1 Polymer, PEMULEN TR-2 polymer, all from the Lubrizol Company), the polymer known under the INCI name Acrylates/Steareth-20 Methacrylate Crosspolymer, which is sold for example under the trade name ACULYN 88 by Rohm and Haas in the form of a 28 to 30 weight percent dispersion in water, polymers known under INCI nomenclature as Acrylates/Palmeth-25 Acrylate Copolymer or Acrylates/Palmeth-20 Acrylate Copolymer which may be available for example from 3V Sigma under the trade name SYNTHALEN W 2000 as a 30 to 32 weight percent emulsion in water, or mixtures thereof.

In an exemplary embodiment, the booster compositions of the instant disclosure comprise: (a) at least one ionic polymer functionalized with at least one carboxylic acid moiety selected from cationic polymers selected from Polyquaternium-91, Polyquaternium-4, Polyquaternium-11, Polyquaternium-16, and Polyquaternium-68, or mixtures thereof; and (b) a least one compound selected from: (b)(i) at least one alkoxysilane of formula (I); (b)(ii) at least one nonionic latex polymer selected from acrylates copolymer (DAITOSOL 5000 AD, Kobo Products, Inc.), polyacrylate-2 crosspolymer (DAITOSOL 5000 SJ, Kobo Products, Inc.), styrene/acrylates copolymer (DAITOSOL 5000 STY, Kobo Products, Inc.), acrylates/ethylhexyl acrylate copolymer (DAITOSOL 4000 SJT, Kobo Products, Inc.), or mixtures thereof; or (b)(iii) a mixture of (b)(i) and (b)(ii).

In an embodiment, the hair care systems of the instant disclosure comprise:
(1) a booster composition comprising:
   (a) at least one ionic polymer functionalized with at least one carboxylic acid moiety selected from bimodal agents, amphoteric polymers, anionic polymers, cationic polymers, or mixtures thereof, and present in an amount of from about 0.2 to about 5 wt %, preferably, from about 0.3 to about 4 wt %;
   (b) optionally, at least one compound present in a total amount of from about 0.15 to about 6 wt %, preferably from about 0.2 to about 5 wt %, and selected from:
      (i) at least one alkoxysilane having at least one solubilizing functional group and at least one amino substituent and selected from a compound of formula (I):

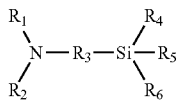

(I)

wherein:
$R_4$ is chosen from halogens, OR', and $R'_1$;
$R_5$ is chosen from halogens, OR'', and $R'_2$;
$R_6$ is chosen from halogens, OR''', and $R'_3$;
$R_1$, $R_2$, $R_3$, R', R'', R''', $R'_2$, and $R'_3$, which may be identical or different, are independently chosen from linear and branched, saturated and unsaturated hydrocarbon-based groups optionally bearing additional chemical groups such as acid or amine groups, it also being possible for $R_1$, $R_2$, R', R'', and R''' to be hydrogens, and at least two of the $R_4$, $R_5$, and $R_6$ groups are different from the $R'_1$, $R'_2$, and $R'_3$ groups, and preferably selected from 3-aminopropyltriethoxysilane;
      (ii) at least one nonionic latex polymer selected from acrylates copolymer, polyacrylate-2 crosspolymer, styrene/acrylates copolymer, acrylates/ethylhexyl acrylate copolymer, or mixtures thereof; and
      (iii) a mixture thereof; and
   (c) at least one thickening agent; and
   (d) a cosmetically acceptable carrier;
   all weights being based on the total composition, including ranges and sub-ranges therebetween; and
(2) at least one hair treatment composition comprising at least one surfactant selected from anionic surfactants, amphoteric surfactants, cationic surfactants, nonionic surfactants, or mixtures thereof.

In an embodiment, the bimodal agent of the above-described hair treatment composition may be selected from polyquaternium-91 (and) polyacrylate-15, polyacrylate-21 (and) acrylates/dimethylaminoethyl methacrylate copolymer, acrylates/ethylhexyl acrylate/hema copolymer (and) acrylates/diethylaminoethyl methacrylate/ethylhexyl acrylate copolymer, polyacrylate-15 (and) polyacrylate-17, polyacrylate-18 (and) polyacrylate-19, polyacrylate-16, or mixtures thereof, and preferably selected from polyquaternium-91 (and) polyacrylate-15.

In an embodiment, the amphoteric polymer of the above-described hair treatment composition may be selected from polyquaternium-22, polyquaternium-39, polyquaternium-47, polyquaternium-53, polyquaternium-61, polyquaternium-69, polyquaternium-86, polyquaternium-95, or mixtures thereof.

In an embodiment, the anionic polymer of the above-described hair treatment composition is selected from Polyacrylate-15, Polyacrylate-21, Polyacrylate-17, Polyacrylate-18, Polyacrylate-19, Acrylates Copolymer, carbomers, acrylates/C10-30 alkyl acrylates crosspolymers, or mixtures thereof.

In an embodiment, the cationic polymer of the above-described hair treatment composition is selected from selected from Polyquaternium-91, Polyquaternium-4, Polyquaternium-11, Polyquaternium-16, and Polyquaternium-68, or mixtures thereof.

In an embodiment, the above-described booster composition comprises at least one compound (b) selected from (b)(i) at least one alkoxysilane.

In an embodiment, the above-described booster composition comprises at least one compound (b) selected from (b)(ii) at least one nonionic latex polymer.

In an embodiment, the above-described booster composition comprises at least one alkoxysilane and at least one nonionic latex polymer.

In various embodiments, any one of the above-described hair-treatment compositions may be in the form of a shampoo, a conditioner, a masque, a leave-in product, or a pre-shampoo treatment product.

When the hair treatment composition is a shampoo, the at least one surfactant includes at least one anionic surfactant selected from alkyl sulfates, alkyl ether sulfates, acyl isethionates, acyl sarcosinates, alkyl sulfonates, alkyl sulfosuccinates, alkyl sulfoacetates, acyl amino acid surfactants other than acyl sarcosinates and selected from acyl taurates, acyl glycinates, acyl glutamates, alkoxylated monoacids, salts thereof, or mixtures thereof; and at least one amphoteric surfactant selected from betaines, alkyl amphoacetates, alkyl amphoproprionates, salts thereof, or mixtures thereof. The hair treatment composition in the form of a shampoo can further comprise at least one nonionic surfactant.

When the hair treatment composition is a conditioner or a masque, the at least one surfactant includes at least one cationic surfactant selected from a quaternary ammonium compound that is a mono or double chain quaternary ammonium compound, wherein each chain independently has from about 14 to about 30 carbon atoms; and the quaternary ammonium compound has a cosmetically acceptable counterion selected from chloride, bromide, and methosulfate. The hair treatment composition in the form of a conditioner or masque can further comprise at least one nonionic surfactant.

When the hair treatment composition is a pre-shampoo treatment or an in-shower treatment product, the at least one surfactant may include at least one nonionic surfactant selected from alkyl polyglucosides, fatty alcohols, alkoxylated fatty alcohols, sorbitan derivatives, glyceryl esters, or mixtures thereof.

In one embodiment, the instant disclosure is directed to a method for cleansing hair comprising applying to the hair any of the above-described hair care systems, wherein the at least one hair treatment composition comprises a shampoo.

In another embodiment, the instant disclosure is directed to a method for conditioning hair comprising applying to the hair any of the above-described hair care systems, wherein the at least one hair treatment composition comprises a conditioner or a masque.

In another embodiment, the instant disclosure is directed to a method for treating or conditioning or protecting hair from damage or styling/shaping hair comprising applying to the hair any of the above-described hair care systems, wherein the at least one hair treatment composition comprises a pre-shampoo treatment product or a leave-in treatment product.

In other embodiments, the instant disclosure is directed to methods for treating hair, the method comprising the steps of:
(1) contacting the hair with any one of the hair care systems of the present disclosure; and
(2) optionally, rinsing the hair;
wherein the method for treating hair includes one or more of:
providing frizz control to hair;
reducing the frizziness of hair;
conditioning hair;
cleansing hair;
providing or improving manageability of hair;
improving ease of combability and detangling;
protecting hair from or reducing damage; and
styling and/or shaping of the hair.

In some embodiments, the methods of the present disclosure involve treating hair according to a layer by layer method, by steps of: (i) contacting hair with the booster composition; and (ii) contacting the hair with the at least one hair treatment composition; wherein either (i) or (ii) is performed as a first step and the other step is performed as a second step. In various methods, the order of steps (i) and (ii) can be reversed. In other embodiments, steps (i) and (ii) may be performed simultaneously, i.e. as an in vivo mixing of the booster composition and hair treatment composition on the hair during application.

In an embodiment, the present disclosure involves a method of treating hair with a hair care system, the method comprising:
(A) combining any of the herein-described booster compositions with at least one hair treatment composition to form a mixture, wherein the at least one hair treatment composition is selected from:
(i) a hair treatment composition comprising a shampoo containing at least one anionic surfactant, and optionally, at least one amphoteric surfactant, in order to form a shampoo mixture; and/or
(ii) a hair treatment composition comprising a conditioner or a masque containing at least one cationic surfactant in order to form a conditioner mixture or a masque mixture; and/or
(iii) a hair treatment composition comprising a pre-shampoo treatment product or an in-shower treatment product or a leave-in treatment product containing at least one cationic surfactant and/or at least one nonionic surfactant in order to form a pre-shampoo treatment mixture or a leave-in treatment mixture; and
(B) contacting hair with the mixture; and
(C) optionally, rinsing the hair.

In various embodiments, the booster composition is combined with one or more hair treatment compositions in a weight ratio of booster composition to hair treatment composition ranging from about 0.2:1 to about 5:1, or about 0.2:1 to about 4:1, or about 0.3:1 to about 4:1, or about 0.4:1 to about 3:1, or about 0.5:1 to about 3;1, or about 1:1 to about 3:1, or about 1.5:1 to about 3:1, or about 2:1 to about 3:1. For example, the weight ratio of booster composition to hair treatment composition may be about 0.5:1, about 0.6:1, about 0.7:1, about 0.8:1, about 0.9:1, about 1:1, about 1.1:1, about 1.2:1, about 1.3:1, about 1.4:1, about 1.5:1, about 1.6:1, about 1.7;1, about 1.8:1, about 1.9:1, about 2:1, about 2.1:1, about 2.2:1, about 2.3:1, about 2.4:1, about 2.5;1, about 2.6;1, about 2.7:1, about 2.8:1, about 2.9:1, or about 3:1.

In various embodiments, the methods include a hair care routine or method such as, but not limited to: a shampoo routine; a shampoo-conditioner routine; a shampoo-masque routine; a shampoo-conditioner-masque routine; a pre-shampoo treatment-shampoo routine; or a shampoo-conditioner-leave-in treatment routine, wherein the routine chosen employs one or more of the shampoo mixture, conditioner mixture, masque mixture, pre-shampoo treatment mixture, and/or leave-in treatment mixture.

Thus, in various embodiments, exemplary and non-limiting methods of treating hair with hair care systems according to the present disclosure may be chosen from the following routines or methods, and variations thereof.

Method (I) comprises steps of:
(1) combining a hair treatment composition comprising a shampoo with a booster composition to form a shampoo mixture;
(2) applying the shampoo mixture to the hair; and
(3) rinsing the shampoo mixture from the hair.

Method (II) comprises steps of:
(1) applying a first hair treatment composition comprising a shampoo to the hair; and
(2) rinsing the shampoo from the hair;
(3) combining a second hair treatment composition comprising a conditioner or masque with a booster composition to form a conditioner mixture or masque mixture;
(4) applying the conditioner mixture or masque mixture to the hair; and
(5) rinsing the conditioner mixture or masque mixture from the hair.

Method (III) comprises steps of:
(1) combining, separately:
a. a first hair treatment composition comprising a shampoo with a booster composition to form a shampoo mixture; and
b. a second hair treatment composition comprising a conditioner or masque with a booster composition to form a conditioner mixture or masque mixture;

(2) applying the shampoo mixture to the hair;
(3) rinsing the shampoo mixture from the hair;
(4) applying the conditioner mixture or masque mixture to the hair; and
(5) rinsing the conditioner mixture or masque mixture from the hair.

Method (IV) comprises steps of:
(1) combining a first hair treatment composition comprising a shampoo with a booster composition to form a shampoo mixture;
(2) applying the shampoo mixture to the hair;
(3) rinsing the shampoo mixture from the hair;
(4) applying a second hair treatment composition comprising a conditioner or masque to the hair; and
(5) rinsing the conditioner or masque from the hair.

Method (V) comprises steps of:
(1) applying a first hair treatment composition comprising a shampoo to the hair;
(2) rinsing the shampoo from the hair;
(3) combining a second hair treatment composition comprising a conditioner or masque with a booster composition in order to form a conditioner mixture or masque mixture;
(4) applying the conditioner mixture or masque mixture to the hair; and
(5) rinsing the conditioner mixture or masque mixture from the hair.

Method (VI) comprises steps of:
(1) combining a first hair treatment composition comprising a pre-shampoo treatment product with a booster composition to form a pre-shampoo treatment mixture;
(2) applying the pre-shampoo treatment mixture to the hair;
(3) optionally, rinsing the hair;
(4) applying a second hair treatment composition comprising a shampoo to the hair; and
(5) rinsing the shampoo from the hair.

Method (VII) comprises steps of:
(1) applying a first hair treatment composition comprising a shampoo to the hair;
(2) rinsing the shampoo from the hair;
(3) applying a second hair treatment composition comprising a conditioner to the hair;
(4) rinsing the conditioner from the hair;
(5) combining a third hair treatment comprising a masque with a booster composition to form a masque mixture;
(6) applying the masque mixture to the hair; and
(7) optionally, rinsing the hair.

The instant disclosure is also directed to multi-component kits comprising any of the above-described hair care systems, and variations thereof. Therefore, in various embodiments, any one of the hair treatment compositions in the kit may be a shampoo, a conditioner, a masque, a leave-in treatment product, or a pre-shampoo treatment product.

In various embodiments, the kit contains one or more separately contained components comprising at least one hair treatment composition according to the disclosure, such as a shampoo, a conditioner, a masque, a leave-in treatment product, or a pre-shampoo treatment product, etc.

In various embodiments, the kit contains two or more separately contained components comprising at least two hair treatment compositions according to the disclosure, such as a shampoo and a conditioner; or a shampoo and a masque; or a shampoo and a leave-in treatment product; or a pre-shampoo treatment product and a shampoo, etc.

In various embodiments, the kit contains three or more separately contained components comprising at least three hair treatment compositions according to the disclosure, such as a shampoo, a conditioner, and a masque; or a shampoo, a conditioner, and a leave-in treatment product; or a shampoo, a masque, and a leave-in treatment product; or a pre-shampoo treatment product, a shampoo, and a conditioner, etc.

In an embodiment, one of the two or more separately contained components includes a first hair treatment composition comprising a shampoo and another of the two or more separately contained components includes a second hair treatment composition comprising a conditioner.

The hair care systems of the instant disclosure are particularly useful for cleansing and conditioning keratinous substrates such as hair. The hair care systems exhibit good cleansing ability, lather, foaming and foam stability, and conditioning properties. In particular, in various embodiments the hair care systems provide anti-frizz properties to hair even at high humidity conditions, as well as a variety of other desirable benefits, for example, smoothness, detangling, suppleness, manageability, and ease of styling and/or shaping. Accordingly, in various embodiments, the hair care systems may be used in methods of cleansing hair, methods of conditioning hair, methods of imparting frizz control and/or manageability to hair, as well as methods of imparting ease of styling and/or shaping of hair.

a) Ionic Polymer Functionalized With at Least One Carboxylic Acid Moiety

The at least one ionic polymer functionalized with at least one carboxylic acid moiety may be selected from bimodal agents, amphoteric polymers, anionic polymers, cationic polymers, or mixtures thereof.

In various embodiments according to the disclosure, the least one ionic polymer functionalized with at least one carboxylic acid moiety is present, as polymeric active material (dry weight basis), in an amount ranging from about 0.1% to about 10% by weight, or from about 0.1% to about 8% by weight, or from about 0.1% to about 6% by weight, including all ranges and sub-ranges therebetween, based on the total weight of the booster composition.

In other various embodiments, the at least one ionic polymer functionalized with at least one carboxylic acid moiety can be employed, as polymeric active material (dry weight basis), in an amount of about 0.10%, 0.15%, 0.18%, 0.2%, 0.25%, 0.30%, 0.33%, 0.37%, 0.40%, 0.45%, 0.5%, 0.55%, 0.6%, 0.67%, 0.70%, 0.75%, 0.8%, 0.85%, 0.90%, 0.95%, 1%, 1.2%, 1.3%, 1.4%, 1.5%, 1.6%, 1.67%, 1.70%, 1.8%, 1.9%, 2%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.7%, 3.8%, 3.9%, 4%, 4.1%, 4.2%, 4.3%, 4.4%, 4.5%, 4.6%, 4.7%, 4.8% 4.9%, 5%, 5.1%, 5.2%, 5.3%, 5.4%, 5.5%, 5.6%, 5.7%, 5.8%, 5.9%, 6%, 6.25%, 6.5%, 6.75%, 7%, 7.25%, 7.5%, 7.75%, 8%, 8.25%, 8.5%, 8.75%, 9%, 9.5% and 10% by weight, based on the total weight of the booster composition.

The bimodal agents, amphoteric polymers, anionic polymers, and cationic polymers of the instant disclosure may be latex or non-latex polymers. They may also be film-forming or non film-forming polymers.

Latex polymers may, in various exemplary embodiments, be chosen from acrylate latex polymers.

When the ionic polymers of the instant disclosure are latex polymers, the latex polymers are provided in the form of aqueous dispersions prior to formulating the compositions of the disclosure. In various embodiments, the aqueous dispersions may be obtained through an emulsion polymerization of monomers wherein the resulting latex polymers have a particle size lower than about 1 micron. In at least one exemplary embodiment, a dispersion prepared by the polymerization in water of one or more monomers having a polymerizable double bond may be chosen. In another exemplary embodiment, the aqueous dispersions obtained through an emulsion polymerization may be spray-dried.

In other embodiments, the latex polymers may be produced from condensation reactions between monomers and subsequently dispersed in an aqueous medium.

Thus, the latex polymers may, in various exemplary embodiments, exist as dispersed polymer particles in a dispersion medium, such as an aqueous dispersion medium. The latex polymers may, in certain embodiments, each be dispersed in independent dispersion media. In yet further embodiments, the latex polymers may be dispersed together in the same dispersion medium.

The dispersion medium comprises at least one solvent chosen from water. The dispersion medium may further comprise at least one solvent chosen from cosmetically acceptable organic solvents. Cosmetically acceptable organic solvents may, in various embodiments, be water-miscible, e.g. capable of forming at 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; and silicones, such as dimethicones, cyclomethicones, and cyclopentasiloxane; as well as mixtures thereof.

In at least one embodiment, the solvent of the dispersion medium consists of water. In other embodiments, the solvent of the dispersion medium consists of water and at least one cosmetically acceptable organic solvent. In further embodiments, the solvent comprises water. In yet further embodiments, the solvent of the dispersion medium primarily comprises water. For example, the solvent of the dispersion medium may, in at least certain exemplary embodiments, comprise greater than 50% water, such as greater than 55% water, greater than 60% water, greater than 65% water, greater than 70% water, greater than 75% water, greater than 80% water, greater than 85% water, greater than 90% water, greater than 95% water, greater than 96% water, greater than 97% water, greater than 98% water, or greater than 99% water.

In embodiments according to the disclosure, the latex polymer (a) particles are not soluble in the solvent of the dispersion medium, i.e. are not water soluble and/or are not soluble in the at least one cosmetically acceptable organic solvent. Accordingly, the latex polymers retain their particulate form in the solvent or solvents chosen.

In at least certain exemplary embodiments, latex polymer (a) particles according to the disclosure may have an average diameter ranging up to about 1000 nm, such as from about 50 nm to about 800 nm, or from about 100 nm to about 500 nm. Such particle sizes may be measured with a laser granulometer (e.g. Brookhaven BI90).

In various embodiments, the latex polymers may, independently, be neutralized, partially neutralized, or unneutralized. In exemplary embodiments where the latex polymers are neutralized or partially neutralized, the particle size may be, for example, greater than about 800 nm. In at least certain embodiments, the particulate form of the latex polymers is retained in the dispersion medium.

By way of non-limiting example only, the latex polymers may be chosen from acrylate latex polymers, such as those resulting from the homopolymerization or copolymerization of ethylenically unsaturated monomers chosen from monomers, (meth)acrylic monomers, (meth)acrylamide monomers and mono- and dicarboxylic unsaturated acids. The term "(meth)acryl" and variations thereof, as used herein, means acryl or methacryl.

The (meth)acrylic monomers may be chosen from, for example, acrylic acid, methacrylic acid, citraconic acid, itaconic acid, maleic acid, fumaric acid, crotonic acid, and maleic anhydride. Additional non-limiting examples of (meth)acrylic monomers include C1-C8 alkyl (meth)acrylic, such as, for example, methyl (meth)acrylic, ethyl (meth)acrylic, propyl (meth)acrylic, isopropyl (meth)acrylic, butyl (meth)acrylic, tert-butyl (meth)acrylic, pentyl(meth) acrylic, isopentyl (meth)acrylic, neopentyl (meth)acrylic, hexyl (meth)acrylic, isohexyl (meth)acrylic, 2-ethylhexyl (meth) acrylic, cyclohexyl (meth)acrylic, isohexyl (meth)acrylic, heptyl (meth)acrylic, isoheptyl (meth)acrylic, octyl (meth) acrylic, isooctyl (meth)acrylic, as well as combinations of any of the above.

The esters of (meth)acrylic monomers may be, by way of non-limiting example, C1-C8 alkyl (meth)acrylates such as methyl (meth)acrylate, ethyl (meth)acrylate, propyl (meth) acrylate, isopropyl (meth)acrylate, butyl (meth)acrylate, tert-butyl (meth)acrylate, pentyl(meth) acrylate, isopentyl (meth)acrylate, neopentyl (meth)acrylate, hexyl (meth)acrylate, isohexyl (meth)acrylate, 2-ethylhexyl (meth)acrylate, cyclohexyl (meth)acrylate, isohexyl (meth)acrylate, heptyl (meth)acrylate, isoheptyl (meth)acrylate, octyl (meth)acrylate, isooctyl (meth)acrylate, allyl (meth)acrylate, and combinations thereof. Additional and non-limiting examples include C1-C8 alkoxy (meth)acrylates, such as methoxy (meth)acrylate, ethoxy (meth)acrylate, propyl oxide (meth) acrylate, isopropyl oxide (meth)acrylate, butyl oxide (meth) acrylate, tert-butyl oxide (meth)acrylate, pentyl oxide (meth) acrylate, isopentyl oxide (meth)acrylate, neopentyl oxide (meth)acrylate. The esters may be, by way of non-limiting example, C2-C6 hydroxy alkyl (meth)acrylates, such as hydroxy ethyl (meth)acrylate, 2-hydroxypropyl (meth)acrylate, glycidyl (meth)acrylate, ethylene glycol di(meth)acrylate, polyethylene glycol mono(meth)acrylate, 1,4-butane diol di(meth)acrylate, 1,6,hexane diol di(meth) acrylate, and any combination thereof. The esters may be, by way of non-limiting example, aryl (meth)acrylates such as benzyl (meth)acrylate, phenyl (meth)acrylate, and any combination thereof. The esters can further contain amino groups such as aminoethyl (meth)acrylate, N,N-dimethyl-aminoethyl (meth)acrylate, N,N-dimethylaminopropyl (meth)acrylate, N,N-dimethylaminodimethylpropyl (meth) acrylate, N,N-diethyleaminoethyl (meth)acrylate, and N,N, N-trimethylaminoethyl (meth)acrylate; and salts of the ethylenic amines.

According to at least certain exemplary embodiments, the alkyl group of the esters may be either fluorinated or perfluorinated, e.g. some or all of the hydrogen atoms of the alkyl group are substituted with fluorine atoms. The monomers can also be fluorine-containing monomers, such as, by way of non-limiting example, trifluoroethyl methacrylate, 2,2,3,3-tetrafluoropropyl methacrylate, 2,2,3,3,4,4-hexafluorobutyl methacrylate, perfluorooctyl methacrylate and perfluorooctyl acrylate; and silicone macromonomers.

The amides of (meth)acrylic monomers can, for example, be made of (meth)acrylamides, and especially N-alkyl (meth)acrylamides, in particular N—(C1-C12) alkyl (meth) acrylates such as N-ethyl (meth)acrylamide, N-t-butyl (meth)acrylamide, N-t-octyl (meth)acrylamide, N-methylol (meth)acrylamide and N-diacetone (meth)acrylamide, and any combination thereof.

The vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate and vinyl t-butyl benzoate, triallyl cyanurate; vinyl halides such as vinyl chloride and vinylidene chloride; aromatic mono- or divinyl compounds such as styrene, α-methylstyrene, chlorostyrene, alkylstyrene, divinylbenzene and diallyl phthalate, and combination thereof. Other non-limiting ionic monomers can include para-styrensulfonic, vinylsulfonic, 2-(meth)acryloyloxyethylsulfonic, 2-(meth)acrylamido-2-methylpropylsulfonic acids.

The list of monomers given is not limiting, and it should be understood that it is possible to use any monomer known to those skilled in the art which includes acrylic and/or vinyl monomers (including monomers modified with a silicone chain).

In at least certain, non-limiting exemplary embodiments, acrylate latex polymers may be chosen from aqueous dispersions of Methacrylic Acid/Ethyl Acrylate copolymer (INCI: Acrylates Copolymer, such as LUVIFLEX® SOFT by BASF), PEG/PPG-23/6 Dimethicone Citraconate/C10-30 Alkyl PEG-25 Methacrylate/Acrylic Acid/Methacrylic Acid/Ethyl Acrylate/Trimethylolpropane PEG-15 Triacrylate copolymer (INCI: Polyacrylate-2 Crosspolymer, such as FIXATE SUPERHOLD™ by Lubrizol), Styrene/Acrylic copolymer (such as Acudyne Shine by Dow Chemical), Ethylhexyl Acrylate/Methyl Methacrylate/Butyl Acrylate/Acrylic Acid/Methacrylic Acid copolymer (INCI: Acrylates/Ethylhexyl Acrylate Copolymer, such as Daitosol 5000SJ, Daito Kasei Kogyo), Acrylic/Acrylates Copolymer (INCI name: Acrylates Copolymer, such as DAITOSOL 5000AD, Daito Kasei Kogyo), Acrylates Copolymers, such as those known under the tradenameunder the tradename LUVIMER® MAE (BASF), or under the tradename BALANCE CR (AKZO NOBEL), Acrylates/Hydroxyesters Acrylates Copolymer, known under the tradename ACUDYNE 180 POLYMER (Dow Chemical), Styrene/Acrylates Copolymer, known under the tradename ACUDYNE BOLD from Dow Chemical, Styrene/Acrylates/Ammonium Methacrylate Copolymer, known under the tradename SYNTRAN PC5620 CG from Interpolymer, or mixtures thereof.

In yet further exemplary and non-limiting embodiments, the film-forming latex polymers may be chosen from carboxyl functional polyurethane latex polymers, such as aqueous polyurethane dispersions. These polyurethanes are conventionally formed by the reaction of prepolymer (i) with a coreactant (ii) to produce a terminated or pendant carboxyl functional polyurethane polymer. The prepolymer (i) may have the structure according to formula (XX):

$R_3$ is chosen from radicals of a low molecular weight diol, optionally substituted with ionic groups or potential ionic groups;

n ranges from about 0 to about 5; and m is greater than about 1.

Suitable dihydroxyl compounds for providing the bivalent radical $R_1$ include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, and polyhydroxy polycarbonates may be chosen. Mixtures of such compounds are also within the scope of the disclosure.

The polyester diol(s) may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

The aliphatic dicarboxylic or polycarboxylic acids may be chosen from, for example: succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecanedioic, 1,3-cyclohexanedicarboxylic, 1,4-cyclohexanedicarboxylic, 2,5-norboranedicarboxylic, diglycolic, thiodipropionic, 2,5-naphthalenedicarboxylic, 2,6-naphthalenedicarboxylic, phthalic, terephthalic, isophthalic, oxanic, o-phthalic, tetrahydrophthalic, hexahydrophthalic or trimellitic acid.

The acid anhydrides may, in further exemplary embodiments, be chosen from o-phthalic, trimellitic or succinic acid anhydride or a mixture thereof. By way of non-limiting example only, the dicarboxylic acid may be adipic acid.

The dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, or mixtures thereof. The cycloaliphatic and/or aromatic dihydroxyl compounds may also be suitable as the dihydric alcohol(s) for the preparation of the polyester polyol(s).

The polyester diols may also be chosen from homopolymers or copolymers of lactones, which are, in at least certain embodiments, obtained by addition reactions of lactones or lactone mixtures, such as butyrolactone, ε-caprolactone and/

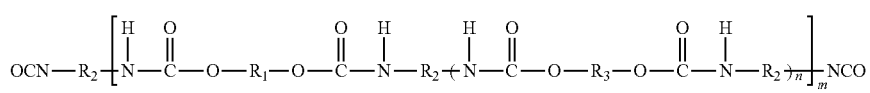

wherein:

$R_1$ is chosen from bivalent radicals of a dihydroxyl functional compound;

$R_2$ is chosen from hydrocarbon radicals of an aliphatic or cycloaliphatic polyisocyanate;

or methyl-ε-caprolactone with the appropriate polyfunctional, e.g. difunctional, starter molecules such as, for example, the dihydric alcohols mentioned above. The corresponding polymers of ε-caprolactone may be chosen in at least some embodiments.

The polyester polyol, e.g. polyester diol, radical $R_1$, may be obtained by polycondensation of dicarboxylic acids, such as adipic acid, with polyols, e.g. diols, such as hexanediol, neopentyl glycol, or mixtures thereof.

The polycarbonates containing hydroxyl groups comprise those known per se, such as the products obtained by reacting diols, such as (1,3)-propanediol, (1,4)-butanediol, and/or (1,6)-hexanediol, diethylene glycol, triethylene glycol, or tetraethylene glycol with diaryl carbonates, for example diphenyl carbonate or phosgene.

Optional polyether polyols may be obtained in any known manner by reacting starting compounds which contain reactive hydrogen atoms with alkylene oxides, such as, for example, ethylene oxide; propylene oxide; butylene oxide; styrene oxide; tetrahydrofuran; or epichlorohydrin, or with mixtures of these alkylene oxides. In at least certain embodiments, the polyethers do not contain more than about 10% by weight of ethylene oxide units. For example, polyethers obtained without addition of ethylene oxide may be chosen.

Polyethers modified with vinyl polymers are also suitable according to various embodiments of the disclosure. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536.

Among the polythioethers which may be chosen include the condensation products obtained from thiodiglycol per se and/or with other glycols, dicarboxylic acids, formaldehyde, aminocarboxylic acids, and/or amino alcohols. The products obtained are either mixed polythioethers, polythioether esters, or polythioether ester amides, depending on the co-components.

Optional polyacetals include but are not limited to the compounds which can be prepared from aldehydes, for example formaldehyde, and from glycols, such as diethylene glycol, triethylene glycol, ethoxylated 4,4'-(dihydroxy)diphenyl-dimethylmethane, and (1,6)-hexanediol. Polyacetals useful according to various non-limiting embodiments of the disclosure can also be prepared by polymerization of cyclic acetals.

Optional polyhydroxy polyesteram ides and polyamines include, for example, the mainly linear condensation products obtained from saturated or unsaturated, polybasic carboxylic acids or anhydrides thereof, and from saturated or unsaturated, polyvalent amino alcohols, from diamines, or from polyamines, as well as mixtures thereof.

Optional monomers for the production of polyacrylates having hydroxyl functionality comprise acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, and 2-isocyanatoethyl methacrylate.

Mixtures of dihydroxy compounds can also be chosen.

Optional polyisocyanates for providing the hydrocarbon-based radical $R_2$ include, for example, organic diisocyanates having a molecular weight ranging from about 100 to about 1500, such as about 112 to about 1000, or about 140 to about 400.

Optional diisocyanates are those chosen from the general formula $R_2(NCO)_2$, in which $R_2$ represents a divalent aliphatic hydrocarbon group comprising from about 4 to 18 carbon atoms, a divalent cycloaliphatic hydrocarbon group comprising from about 5 to 15 carbon atoms, a divalent aromatic hydrocarbon group comprising from about 7 to 15 carbon atoms, or a divalent aromatic hydrocarbon group comprising from about 6 to 15 carbon atoms. Examples of the organic diisocyanates which may be chosen include, but are not limited to, tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanatomethyl-3,5,5-trimethylcyclohexane (isophorone diisocyanate or IPDI), bis(4-isocyanatocyclohexyl)-methane, 1,3-bis(isocyanatomethyl)-cyclohexane and 1,4-bis(isocyanatomethyl)cyclohexane and bis(4-isocyanato-3-methylcyclohexyl)-methane. Mixtures of diisocyanates can also be used.

In at least certain embodiments, diisocyanates are chosen from aliphatic and cycloaliphatic diisocyanates. For example, 1,6-hexamethylene diisocyanate, isophorone diisocyanate, and dicyclohexylmethane diisocyanate, as well as mixtures thereof may be chosen.

The use of diols, for example low molecular weight diols, R3, may in at least certain embodiments allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain exemplary embodiments, the compounds contain only aliphatic groups. The diols that may be chosen may optionally have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis(4-hydroxyphenyl)propane), hydrogenated bisphenol A (2,2-bis(4-hydroxycyclohexyl)-propane), or mixtures thereof. For example, $R_3$ may be derived from neopentyl glycol.

Optionally, the low molecular weight diols may contain ionic or potentially ionic groups. Suitable low molecular weight diols containing ionic or potentially ionic groups may be chosen from those disclosed in U.S. Pat. No. 3,412,054. In various embodiments, compounds may be chosen from dimethylolbutanoic acid (DMBA), dimethylolpropionic acid (DMPA), and carboxyl-containing caprolactone polyester diol. If low molecular weight diols containing ionic or potentially ionic groups are chosen, they may, for example, be used in an amount such that less than about 0.30 meq of —COON is present per gram of polyurethane in the polyurethane dispersion. In at least certain exemplary and non-limiting embodiments, the low molecular weight diols containing ionic or potentially ionic groups are not used.

Coreactants (ii) are compounds containing functional groups such as hydroxy or amine groups, preferably primary amine, adapted to react with isocyanate groups in preference to the carboxyl group according to the formula:

X—$R_4$-X wherein X is chosen from OH and NH2, and $R_4$ represents a divalent aliphatic or cycloaliphatic or aromatic hydrocarbon group, optionally substituted with ionic groups or potentially ionic groups. In various embodiments, compounds may optionally be chosen from alkylene diamines, such as hydrazine, ethylenediamine, propylenediamine, 1,4-butylenediamine, and piperazine. In various embodiments, compounds may optionally be chosen from alkylene diols, such as ethylene glycol, 1,4-butanediol (1,4-BDO or BDO), 1,6-hexanediol.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Special compounds may be chosen from dimethylolbutanoic acid (DMBA), dimethylolpropionic acid (DMPA), or carboxyl functional polyester comprising excess equivalents of dicarboxylic acid reacted with lesser equivalents of glycol or carboxyl-containing caprolactone polyester diol.

In various embodiments of formula (XX), R1, R2, R3, R4 can have at least one carboxyl group independently.

By way of non-limiting example, such latexes include, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as LUVISET® P.U.R, BASF), a copolymer of hexylene glycol, neopentyl glycol, adipic acid, saturated methylene diphenyldiisocyanate and dimethylolpropanoic acid monomers (INCI name: polyurethane 2), a copolymer of PPG-17, PPG-34, isophorone diisocyanate and dimethylolpropanoic acid monomers (INCI name: polyurethane 4), a copolymer of isophthalic acid, adipic acid, hexylene glycol, neopentyl glycol, dimethylolpropanoic acid, isophorone diisocyanate and bis-ethylaminoisobutyl-dimethicone monomers (INCI name: polyurethane 6), Isophorone diisocyanate, cyclohexanedimethanol, dimethylol butanoic acid, polyalkylene glycol and N-methyl diethanolamine copolymer (INCI name: polyurethane 10), Trimethylolpropane, neopentyl glycol, dimethylol propionic acid, polytetramethylene ether glycol and isocyanato methylethylbenzene copolymer (INCI name: polyurethane 12), Isophorone diisocyanate, dimethylol propionic acid, and 4,4'-isopropylidenediphenol reacted with propylene oxide, ethylene oxide and PEG/PPG-17/3 copolymer (INCI name: polyurethane 14), Isophorone diisocyanate, adipic acid, triethylene glycol and dimethylolpropionic acid copolymer (INCI name: polyurethane 15), 2-Methyl-2,4-pentanediol, polymer with 2,2-dimethyl-1,3-propanediol, hexanedioic acid, methylenedicyclohexanediisocyanate and 2,2-di(hydroxymethyl)propanoic acid, hydrolysed, tris(2-hydroxyethyl)amine salts, reaction products with 1,2-ethanediamine (INCI name: polyurethane 17), Polyurethane-27 is a complex polymer that is formed by the reaction of Polyperfluoroethoxymethoxy Difluorohydroxyethyl Ether and isophorone diisocyanate (IPDI) to form a prepolymer. The prepolymer is further reacted with the triethylamine salt of 3-hydroxy-2-(hydroxymethyl)-2-methyl-1-propionic acid (INCI name: polyurethane 27), a complex polymer formed by reacting dimethylolpropionic acid and a polyester composed of Adipic Acid, Hexylene Glycol, Neopentyl Glycol with methylene dicyclohexyldiisocyanate (SMDI) to form a prepolymer. The prepolymer is neutralized with triethylamine and then chain-extended with hydrazine (INCI name: polyurethane 33).

In some embodiments, the latex polymers of the present invention are film-forming latex polymers.

In certain other embodiments, the latex polymers of the present invention are non film-forming latex polymers.

As used herein, a film-forming polymer is meant to include a polymer that is capable, by itself or in the presence of an auxiliary film-forming agent, of forming a macroscopically substantially continuous or continuous film that adheres to keratin materials, and preferably a cohesive film, better still, a film whose cohesion and mechanical properties are such that said film can be isolated and manipulated individually, for example, when said film is prepared by pouring onto a non-stick surface such as Teflon-coated or silicone-coated surface. In addition, as used herein, a non-film-forming polymer is meant to include a polymer which will not form a film at ambient temperature or below, or in other words, will only form a film at temperatures above ambient. For purposes of this disclosure, ambient temperature is taken as being below 40° C. such as in the range of 15° C. to 30° C.

By way of non-limiting example only, the latex polymers may be chosen from at least one carboxyl functional silicone latex polymer.

The carboxyl functional silicone latex polymer can be an organopolysiloxane comprising:

(A) a compound having the following formula, Unit (A):

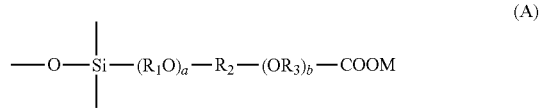

wherein:

$R_1$ and $R_3$ independently denote a linear or branched alkylene radical containing from 2 to 20 carbon atoms, $R_2$ denotes a linear or branched alkylene radical containing from 1 to 50 carbon atoms which can comprise a hydroxyl group, a represents 0 or 1, b is a number ranging from 0 to 200, and M denotes hydrogen, an alkali metal or alkaline-earth metal, NH4 or a quaternary ammonium group such as a mono-, di-, tri- or tetra($C_1$-$C_4$ alkylammonium) group, and optionally substituted divalent aromatic groups, such as groups of formula (A'):

and groups of formula (A"):

$R_1$ and $R_3$ can denote, for example, ethylene, propylene or butylene;

(B) a group comprising at least one pyrrolidone carboxylic acid unit having the following formula, unit (B):

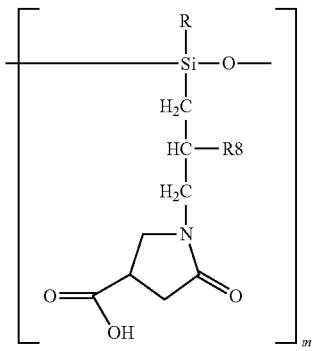
(B)

wherein:

R is selected from methyl or phenyl;

R8 is hydrogen or methyl; and m is an integer from 1 to 1000, (C) a group comprising at least one polyvinyl acid/ester unit (C) resulting from the polymerization of Divinyl-PDMS, Crotonic Acid, Vinylacetate, and Vinyl Isoalkylester; and combinations of (A), (B) and (C).

Suitable silicone latex polymers include, for example, for example, a silicone comprising at least one carboxylic acid group chosen from organopolysiloxanes of formula (IA):

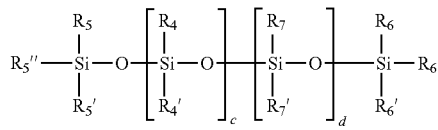
(IA)

wherein:

the radicals $R_4$ and $R_4'$ are identical to or different from each other and are chosen from a linear or branched $C_1$-$C_{22}$ alkyl radical, a $C_1$-$C_{22}$ alkoxy radical, and a phenyl radical, the radicals $R_5$, $R_5'$, $R_5''$, $R_6$, $R_6'$, $R_6''$, $R_7$, and $R_7'$ are identical to or different from each other and are chosen from a linear or branched $C_1$-$C_{22}$ alkyl radical, a $C_1$-$C_{22}$ alkoxy radical, a phenyl radical, a radical —$(R_1O)_a$—$R_2$—$(OR_3)_b$—COOM, a radical containing pyrrolidone carboxylic acid, and a radical of polyvinyl acid/ester;

wherein at least one of the radicals $R_5$, $R_6$ and $R_7$ is a radical chosen from a radical —$(R_1O)_a$—$R_2$—$(OR_3)_b$—COOM, a radical containing pyrrolidone carboxylic acid, and a radical of polyvinyl acid/ester; wherein $R_1$, $R_2$, $R_3$, a, b, and M have the same meaning as described in Unit (A) above; and wherein c and d are integers from 0 to 1000, the sum c+d preferably ranging from 1 to 1000, or from 2 to 1000.

Among the compounds of formula (IA) that comprise at least one unit (A), the preferred ones are the compounds of formula (IIA) below:

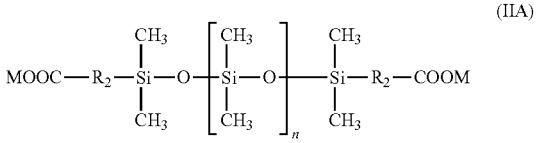
(IIA)

wherein $R_2$ and M have the same meaning as described in Unit (A) above, and n is an integer from 1 to 1000.

Other preferred compounds of formula (IA) are the ones of formula (IIIA):

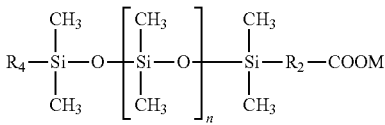
(IIIA)

wherein $R_2$, $R_4$, and M have the same meaning as in Unit (A) above, and n is an integer from 1 to 1000.

Other preferred compounds of formula (IA) are the ones of formula (IVA):

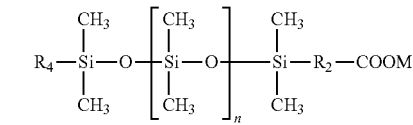
(IVA)

in which X is a radical —$(R_1O)_a$—$R_2$—$(OR_3)_b$—COOM, wherein $R_1$, $R_2$, $R_3$, a, b, and M have the same meaning as described in Unit (A) above, and n is an integer from 1 to 1000.

Even more particularly, the compounds of formula (IVA) in which a and b are equal to 0 and $R_2$ is a linear or branched $C_2$-$C_{12}$ alkylene group such as $(CH_2)_9$, $(CH_2)_{10}$, or —CH($CH_3$)— are preferred.

Among the compounds of formula (IA) that contain unit (B), the preferred ones are the compounds of formula (VA) below:

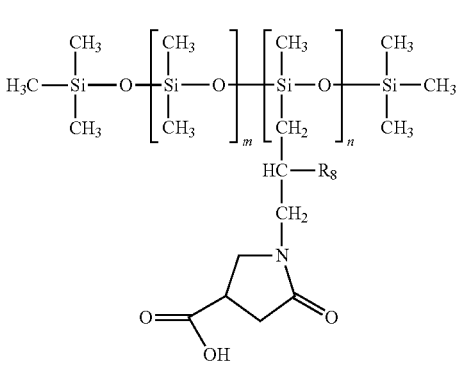
(VA)

wherein $R_8$ and m are as defined in Unit (B) above, and n is an integer from 1 to 1000.

Among the organopolysiloxanes of formula (IA) that contain polyvinyl acid/ester Unit (C), the preferred ones are cross-linked anionic copolymers comprised of organic polymer blocks and silicone blocks, resulting in a multiblock polymer structure. In particular, the silicone-organic polymer compound of the present invention may be chosen from cross-linked anionic copolymers comprising at least one cross-linked polysiloxane structural unit. An example of such a branched multi-block carboxy silicone polymer is BELSIL P1101 (may also be known under the tradename BELSIL P101) (INCI name: Crotonic Acid/Vinyl C8-12 Isoalkyl Esters/VA/Bis-Vinyldimethicone Crosspolymer, also known by the technical name of Crotonic Acid/Vinyl C8-12 Isoalkyl Esters/VA/divinyldimethicone Crosspolymer) from Wacker Chemie AG.

Additional suitable carboxysilicone polymers are described, for example, in patent applications WO 95/23579 and EP-A-0,219,830, which are hereby incorporated by reference in their entirety.

Bimodal Agent

A bimodal agent as used herein refers to a bimodal polymer composition or blend prepared by polymerizing monomers resulting in a first polymer of a cationic character and a second polymer of an anionic character. Thus, the bimodal agent comprises a polymeric component having at least one anionic functionality and a polymeric component having at least one cationic functionality.

In an embodiment, the bimodal agent is a film forming agent.

In an embodiment, the bimodal agent forms an interpenetrating network containing multiple functionalities (for example, cationic and anionic functionalities) which is reversibly cross-linked, at least partially, through the multiple functionalities.

In an embodiment, the bimodal film forming agent comprises at least one acrylic acid-based, (meth)acrylic acid-based, acrylate-based or (meth)acrylate-based monomer having anionic and/or cationic functionalities. Suitable polymers or copolymers include, but are not limited to, polymers comprising polyacrylates such as those identified in the International Cosmetic Ingredient Dictionary and Handbook (9th ed. 2002) such as, for example, polyacrylate-1, polyacrylate-2, polyacrylate-3, polyacrylate-4, polyacrylate-16, polyacrylate-17, polyacrylate-18, polyacrylate-19, etc. Such (co)polymers, or similar (co)polymers, can be combined individually or with other (co)polymers in such a way to form suitable bimodal film forming agents having both cationic and anionic functionalities.

In an embodiment, the bimodal agent(s) of the instant disclosure includes ionic latex polymer(s) that are also called amphoteric latex polymers in the instant disclosure.

Suitable exemplary amphoteric latex polymers are set forth in Table A below.

Amphoteric Polymer

The amphoteric polymers of the instant disclosure may, for example, be selected from polyquaternium-22, polyquaternium-39, polyquaternium-47, polyquaternium-53, polyquaternium-61, polyquaternium-69, polyquaternium-86, polyquaternium-95, or mixtures thereof.

Anionic Polymer

In an embodiment, the at least one ionic polymer functionalized with at least one carboxylic acid moiety is selected from at least one anionic polymer that is an anionic latex polymer or an anionic non-latex polymer.

In an embodiment, the at least one anionic polymer includes at least one anionic latex polymer selected from Polyacrylate-15, Polyacrylate-21, Polyacrylate-17, Polyacrylate-18, Polyacrylate-19, a branched anionic acrylate copolymer Polyacrylate-2 Crosspolymer (FIXATE SUPERHOLD polymer), Acrylates Crosspolymer-3 (FIXATE FREESTYLE Polymer), Polyacrylate-14 (FIXATE PLUS Polymer), and those sold under the SYNTRAN series as commercially available from Interpolymer such as Acrylates Copolymer (SYNTRAN 5190), Styrene/Acrylates/Ammonium Methacrylate Copolymer (SYNTRAN 5760), and Ammonium Acrylates Copolymer (SYNTRAN KL-219C) and polyurethane-1 (e.g. LUVISET P.U.R. from BASF), polyurethane-34 (BAYCUSAN from Bayer), polyurethane-14/AMP-acrylates copolymer blend (e.g. DYNAMX (from Akzo Nobel), acrylates copolymers of two or more monomers of (meth)acrylic acid or one of their simple esters (e.g. BALANCE CR from Akzo Nobel), or mixtures thereof.

In an embodiment, the at least one anionic polymer includes at least one anionic non-latex polymer selected from copolymers of acrylic acid or acrylic esters.

In an embodiment, the anionic non-latex polymers are selected from Polyacrylate-15, Polyacrylate-21, Polyacrylate-17, Polyacrylate-18, Polyacrylate-19, the acrylic acid/ethyl acrylate/N-tert-butylacrylamide terpolymers sold in particular under the name ULTRAHOLD STRONG by BASF, copolymers derived from crotonic acid, such as the vinyl acetate/vinyl tert-butylbenzoate/crotonic acid terpolymers and the crotonic acid/vinyl acetate/vinyl neododecanoate terpolymers sold in particular under the name RESIN 28-29-30 by National Starch, polymers derived from maleic, fumaric or itaconic acids or anhydrides with vinyl esters, vinyl ethers, vinyl halides, phenylvinyl derivatives, or acrylic acid and its esters, such as the methyl vinyl ether/monoesterified maleic anhydride copolymers sold, for example, under the name GANTREZ by ISP, the copolymers of methacrylic acid and of methyl methacrylate sold under the name EUDRAGIT L by Rohm Pharma, the copolymers of methacrylic acid and of ethyl acrylate sold

TABLE A

| Latex | INCI Name | Sold By |
|---|---|---|
| | Amphoteric Latex Polymers | |
| SYNTRAN PC5330 | Polyquaternium-91 (and) Polyacrylate-15 | Interpolymer |
| SYNTRAN PC5500 | Polyquaternium-91 (and) Polyacrylate-15 | Interpolymer |
| SYNTRAN PC5100-CG | Polyacrylate-21 (and) Acrylates/Dimethylaminoethyl Methacrylate copolymer | Interpolymer |
| SYNTRAN PC5775 | Acrylates/ethylhexyl acrylate/hema copolymer (and) acrylates/diethylaminoethyl methacrylate/ethylhexyl acrylate copolymer | Interpolymer |
| SYNTRAN PC5227 CG | Polyacrylate-15 (and) polyacrylate-17 | Interpolymer |
| SYNTRAN 5112 | Polyacrylate-16 | Interpolymer |
| SYNTRAN PC5107 | Polyacrylate-18 (and) polyacrylate-19 | Interpolymer |
| SYNTRAN PC5117 | Polyacrylate-18 (and) polyacrylate-19 | Interpolymer | under the name LUVIMER MAEX or MAE by BASF, the vinyl acetate/crotonic acid copolymers sold under the name LUVISET CA 66 by BASF and the vinyl acetate/crotonic acid copolymers grafted by polyethylene glycol sold under the name ARISTOFLEX A by BASF, those anionic polymers as sold under the FIXATE series as commercially available from Lubrizol, such as a branched block anionic polymer sold as FIXATE G-100, those sold under the CARBOPOL series as commercially available from Lubrizol such as Acrylates Crosspolymer-4 (CARBOPOL AQUA SF-2), Acrylates Crosspolymer-4 (CARBOPOL AQUA CC), Acrylates Copolymer (CARBOPOL AQUA SF-1) carbomers (trade names CARBOPOL 980, CARBOPOL 981, CARBOPOL 5984, CARBOPOL ETD 2050 and CARBOPOL Ultrez-10 Polymer, all from the Lubrizol Company), acrylates/C10-30 alkyl acrylates crosspolymers (trade names CARBOPOL 1382, CARBOPOL ETD 2020, PEMULEN TR-1 Polymer, PEMULEN TR-2 polymer, all from the Lubrizol Company), the polymer known under the INCI name Acrylates/Steareth-20 Methacrylate Crosspolymer, which is sold for example under the trade name ACULYN 88 by Rohm and Haas in the form of a 28 to 30 weight percent dispersion in water, polymers known under INCI nomenclature as Acrylates/Palmeth-25 Acrylate Copolymer or Acrylates/Palmeth-20 Acrylate Copolymer which may be available for example from 3V Sigma under the trade name SYNTHALEN W 2000 as a 30 to 32 weight percent emulsion in water, or mixtures thereof.

In various exemplary embodiments, the ionic polymers of the instant disclosure selected from anionic polymers are latex polymers chosen from aqueous dispersions of the following, including mixtures thereof, set forth in Table B.

TABLE B

| Latex | INCI Name | Sold By |
|---|---|---|
| | Anionic Latex Polymers | |
| LUVIFLEX Soft | Acrylates copolymer | BASF |
| FIXATE Superhold | Polyacrylate-2 Crosspolymer | Lubrizol |
| NEOCRYL A-1120 | Styrene/Acrylic copolymer | DSM |
| ACULYN 33 | Acrylates Copolymer | Dow Chemical |
| LUVIMER MAE | Acrylates copolymer | BASF |
| BALANCE CR | Acrylates copolymer | Akzo Nobel |
| ACUDYNE DHR | Acrylates/hydroxyesters Acrylates Copolymer | Dow Chemical |
| ACUDYNE 180 POLYMER | Acrylates/Hydroxyesters Acrylates Copolymer | Dow Chemical |
| ACUDYNE SHINE | Styrene/Acrylates Copolymer | Dow Chemical |
| ACUDYNE BOLD | Styrene/Acrylates Copolymer | Dow Chemical |
| JONCRYL 77 | Styrene/Acrylates Copolymer | BASF |
| SYNTRAN PC5620 CG | Styrene/Acrylates/Ammonium Methacrylate Copolymer | Interpolymer |
| SYNTRAN 5009-CG | Styrene/Acrylates/Ammonium Methacrylate Copolymer | Interpolymer |
| SYNTRAN 5190-CG | Acrylates Copolymer | Interpolymer |
| SYNTRAN 5760-CG | Styrene/Acrylates/Ammonium Methacrylate Copolymer | Interpolymer |
| SYNTRAN 5620 | Styrene/Acrylates/Ammonium Methacrylate Copolymer | Interpolymer |
| SYNTRAN 5762 | Styrene/Acrylates/Ammonium Methacrylate Copolymer | Interpolymer |
| SYNTRAN 5288 | Ethylene/acrylic acid copolymer (and) styrene/acrylates copolymer | Interpolymer |
| SYNTRAN PC5208 | Polyacrylate-15 | Interpolymer |
| ACULYN 28 | Acrylates/Beheneth-25 Methacrylate Crosspolymer Copolymer | Dow Chemical |
| ACULYN 88 | Acrylates/Steareth-20-25 Methacrylate Crosspolymer Copolymer | Dow Chemical |
| DERMACRYL AQF | Acrylic Copolymer | Akzo Nobel |
| DAITOSOL 5500 GM | Acrylates/Ethylhexyl Acrylate copolymer | Kobo Products Inc. |
| DAITOSOL 3000 SLPN | Acrylates Copolymer | Kobo Products Inc. |
| DAITOSOL 3000VP3 | Acrylates Copolymer | Kobo Products Inc. |
| DAITOSOL 5000 PO | Acrylates/Ethylhexyl Acrylate copolymer | Kobo Products Inc. |
| DAITOSOL U9-40 GM | Polyurethane-1, Acrylates Copolymer | Kobo Products Inc. |

Cationic Polymer

In various exemplary embodiments, the at least one cationic polymer may be selected from Polyquaternium-91, Polyquaternium-4, Polyquaternium-11, Polyquaternium-16, and Polyquaternium-68, or mixtures thereof.

b) Compound Selected from Alkoxysilane and a Nonionic Latex Polymer

The booster composition may optionally comprise at least one compound (b), which may be chosen from: (b)(i) at least one alkoxysilane; (b)(ii) at least one nonionic latex polymer; and (b)(iii) mixtures thereof.

When present, in various embodiments the at least one compound (b) may be present in a total amount of from about 0.05 to about 10 wt %, or from about 0.1 to about 8 wt %, or from about 0.15 to about 6 wt %, or from about 0.2 to about 5 wt %, of the booster composition, including ranges and sub-ranges therebetween.

In one or more embodiments, the at least one compound (b) which can be selected from at least one alkoxysilane and/or at least one nonionic latex polymer is present in a total amount of from about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, and 10 wt % of the booster composition.

Alkoxysilane

The hair treatment compositions described herein may, in various exemplary embodiments, comprise at least one alkoxysilane.

In an embodiment, the at least one alkoxysilane has at least one solubilizing functional group and at least one amino substituent. In one or more embodiments, the alkoxysilane is cationic. The cationic alkoxysilane may be neutralized by one or more acids present in the composition.

In some embodiments, the composition may comprise more than one alkoxysilane. In further embodiments any additional alkoxysilanes may be neutralizable. As used herein, a "neutralizable" alkoxysilane means that the compound contains neutralizable moieties such as amine and thiol groups. In some embodiments, the additional alkoxysilanes may be non-neutralizable. As used herein, a "non-neutralizable" alkoxysilane means that the alkoxysilane does not contain such neutralizable moieties.

The at least one alkoxysilane may be chosen from organosilanes comprising one, two, or three silicon atoms, such as one or two silicon atoms. They may also comprise at least one basic chemical function. The at least one basic chemical functional group may correspond to any function that confers a basic nature on the silicon compound, and may be, for instance, an amine function such as a primary, secondary, or tertiary amine function. The basic chemical function of the alkoxysilane compounds according to the present disclosure may optionally comprise other functions, such as another amine function, an acid function, or a halogen function.

The at least one alkoxysilane that may be present in the compositions according to the present disclosure can also comprise one or more hydrolysable or hydroxyl groups per molecule (i.e., solubilizing functional groups). The hydrolysable or solubilizing functional groups are chosen, for example, from alkoxy, aryloxy, and halogen groups. They may also optionally comprise other chemical functions such as acid functions.

According to various exemplary embodiments, the at least one alkoxysilane present in the compositions disclosed herein is chosen from the entities of formula (I):

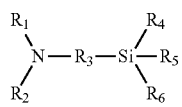

(I)

wherein:
$R_4$ is chosen from halogens, OR', and $R'_1$;
$R_5$ is chosen from halogens, OR", and $R'_2$;
$R_6$ is chosen from halogens, OR''', and $R'_3$;
$R_1$, $R_2$, $R_3$, R', R", R''', $R_2'$, and $R_3'$, which may be identical or different, are independently chosen from linear and branched, saturated and unsaturated hydrocarbon-based groups optionally bearing additional chemical groups such as acid or amine groups, it also being possible for $R_1$, $R_2$, R', R" and R''' to be hydrogens, and at least two of the $R_4$, $R_5$, and $R_6$ groups are different from the $R_2'$, and $R'3$ groups;

or from the entities of formula (Ia):

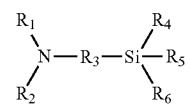

(Ia)

wherein:
$R_4$ is chosen from OR' groups;
$R_5$ is chosen from OR" groups;
$R_6$ is chosen from OR" groups;
$R_1$ and $R_2$ are chosen from hydrogen;
$R_3$, R', R", and R''', which may be identical or different, are chosen from linear and branched, saturated and unsaturated hydrocarbon groups, optionally bearing at least one additional chemical group, wherein R', R", and R" may also be chosen from hydrogen.

In at least one embodiment, the $R_1$, $R_2$, $R'_1$, $R'_1$, $R'_2$, $R'_3$, R", and R''' groups are chosen from $C_1$-$C_{12}$ alkyl, $C_5$-$C_{14}$ aryl, $(C_1$-$C_8)$alkyl$(C_5$-$C_{14})$aryl, and $(C_1$-$C_{14})$aryl$(C_1$-$C_8)$alkyl radicals.

In at least one embodiment, the $R_3$ group is chosen from $C_1$-$C_{12}$ alkylene, optionally substituted with an amino group, $C_5$-$C_{14}$ arylene, $(C_1$-$C_8)$alkylene$(C_5$-$C_{14})$arylene, and $(C_5$-$C_{14})$arylene$(C_1$-$C_8)$alkylene radicals.

According to another embodiment, the at least one alkoxysilane corresponding to the formulae (I) or formula (Ia) is chosen from, for instance, 3-aminopropyltriethoxysilane, 3-aminopropylmethyldiethoxysilane, N-(2-aminoethyl)-3-aminopropylltriethoxysilane and 3-(2-aminoethylamino) propylmethyldiethoxysilane.

According to yet another embodiment, the at least one alkoxysilane with at least one solubilizing functional group and at least one amino substituent that is used according to the present disclosure is chosen from the entities of formula (II):

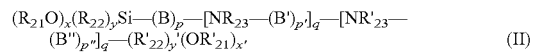

(II)

wherein:
$R_{21}$, $R_{22}$, $R'_{21}$, and $R'_{22}$, which may be identical or different, are independently chosen from linear and branched, saturated and unsaturated hydrocarbon-based chains optionally comprising at least one heteroatom, optionally interrupted or substituted with at least one group chosen from ether, ester, amine, amide, carboxyl, hydroxyl, and carbonyl groups;
x is an integer ranging from 1 to 3;
y=3-x;
x' is an integer ranging from 1 to 3;
y'=3-x';
p=0 or 1;
p'=0 or 1;
p"=0 or 1;
q=0 or 1;
q'=0 or 1;
B, B', and B", which may be identical or different, are independently chosen from linear and branched $C_1$-$C_{20}$ alkylene divalent radicals; and
$R_{23}$ and $R'_{23}$, which may be identical or different, are independently chosen from hydrogen atoms, and linear and branched, saturated and unsaturated hydrocarbon-based chains optionally comprising at least one heteroatom, optionally interrupted or substituted with at least one group chosen from ether, $C_1$-$C_{20}$ alkyl ester, amine, carboxyl, alkoxysilane, $C_6$-$C_{30}$ aryl, hydroxyl and carbonyl groups, or a heterocyclic or nonheterocyclic aromatic ring optionally substituted with at least one group chosen from $C_3$-$C_{20}$ alkyl ester, amine, amide, carboxyl, alkoxysilane, hydroxyl, carbonyl and acyl groups, wherein at least q or q' is other than zero.

As explained above, $R_{21}$, $R_{22}$, $R'_{21}$, $R'_{22}$, $R_{23}$, and $R'_{23}$, which may be identical or different, are independently chosen from hydrocarbon-based chains. As used herein, a "hydrocarbon-based chain" is intended to mean a chain containing 1 to 30 carbon atoms, such as 1 to 20 carbon atoms, or 1 to 10 carbon atoms.

In at least one embodiment, the aromatic ring contains from 6 to 30 carbon atoms, for example, an optionally substituted phenyl radical.

According to at least one embodiment, $R_{21}$=$R'_{21}$; $R_{22}$=$R'_{22}$; x=x'; y=y'; p=p'; B=B'; q=1, and q'=0.

In at least one embodiment, the at least one alkoxysilane with at least one solubilizing functional group and at least one amino substituent is chosen from the entities of formula (II), wherein: $R_{21}$, $R_{22}$, $R'_{21}$, and $R'_{22}$, which may be identical or different, are independently chosen from $C_1$-$C_4$alkyl groups; p=p'=1; B and B', which may be identical or different, are independently chosen from linear $C_1$-$C_4$ alkylene groups, and $R_{23}$ is hydrogen.

For example, the at least one alkoxysilane with at least one solubilizing functional group and at least one amino substituent may comprise a substituent comprising a secondary amine function, such as the bis[3-(triethoxysilyl)propyl]amine of formula $(CH_3CH_2O)_3$—$Si(CH_2)_3NH(CH_2)_3Si(OCH_2CH_3)_3$, proposed by the company Fluorochem, the bis[trimethoxysilylpropyl]amine of formula $(CH_3O)_3$—$Si(CH_2)_3NH(CH_2)_3Si(OCH_3)_3$, proposed by the company Gelest, the bis[methyldiethoxysilylpropyl]amine of formula $(CH_3CH_2O)_2CH_3Si(CH_2)_3NH(CH_2)_3SiCH_3(OCH_2CH_3)_2$, proposed by the company Gelest, and the bis[3-trimethoxysilylpropyl]ethylenediamine of formula $(CH_3O)_3Si(CH_2)_3NH(CH)_2NH(CH_2)_3Si(OCH_3)_3$, proposed by the company Gelest. In at least one embodiment of the present disclosure, bis[3-(triethoxysilyl)propyl]amine and bis[methyldiethoxysilylpropyl]amine are used.

According to another embodiment, the at least one alkoxysilane with at least one solubilizing functional group and at least one amino substituent is chosen from the entities of formula (III):

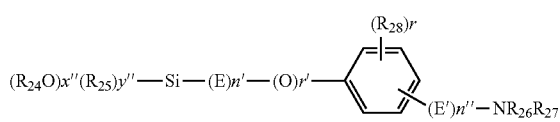
(III)

wherein:

$R_{24}$ and $R_{25}$, which may be identical or different, are independently chosen from linear and branched, saturated and unsaturated hydrocarbon-based chains optionally comprising at least one heteroatom, optionally interrupted or substituted with at least one group chosen from ether, ester, amine, amide, carboxyl, hydroxyl and carbonyl groups;

x''=2 or 3;

y''=3-x'';

n'=0 or 1;

n''=0 or 1;

E and E', which may be identical or different, are independently chosen from linear and branched $C_1$-$C_{20}$ alkylene divalent radicals;

$R_{26}$ and $R_{27}$, which may be identical or different, are independently chosen from a hydrogen atom and linear and branched, saturated and unsaturated hydrocarbon-based chains optionally comprising at least one heteroatom, optionally interrupted or substituted with at least one group chosen from ether, $C_1$-$C_{20}$ alkyl ester, amine, carboxyl, alkoxysilane, $C_6$-$C_{30}$ aryl, hydroxyl and carbonyl groups, or a heterocyclic or nonheterocyclic aromatic ring optionally substituted with at least one group chosen from $C_1$-$C_{20}$ alkyl ester, amine, amide, carboxyl, alkoxysilane, hydroxyl, carbonyl and acyl groups;

r is an integer ranging from 0 to 4;

r'=0 or 1; and each instance of $R_{28}$ is independently chosen from a hydrogen atom and linear and branched, saturated and unsaturated, $C_1$-$C_{10}$, hydrocarbon-based chains optionally comprising at least one heteroatom, optionally interrupted or substituted with at least one group chosen from ether, $C_1$-$C_{20}$ alkyl ester, amine, carboxyl, alkoxysilane, $C_6$-$C_{30}$ aryl, hydroxyl and carbonyl groups, or a heterocyclic or nonheterocyclic aromatic ring optionally substituted with at least one group chosen from $C_1$-$C_{20}$ alkyl ester, amine, amide, carboxyl, alkoxysilane, hydroxyl, carbonyl and acyl groups.

As explained above, $R_{24}$, $R_{25}$' $R_{26}$ and $R_{27}$ are each independently chosen from hydrocarbon-based chains. As used herein, a "hydrocarbon-based chain" is intended to mean a chain containing 1 to 30 carbon atoms, such as 1 to 20 carbon atoms, or 1 to 10 carbon atoms.

In at least one embodiment, the aromatic ring contains from 6 to 30 carbon atoms, for example an optionally substituted phenyl radical.

The at least one alkoxysilane with at least one solubilizing functional group and at least one amino substituent of formula (III), may be chosen wherein:

$R_{24}$ is a C1-C4 alkyl;

x''=3;

n'=n''=1;

r=r'=0; and $R_{26}$ and $R_{27}$, which may be identical or different, are independently chosen from a hydrogen atom and groups chosen from $C_1$-$C_4$ alkyl, $C_1$-$C_4$ hydroxyalkyl, and $C_1$-$C_4$ aminoalkyl groups.

In at least one embodiment, the at least one alkoxysilane comprising at least one basic functional group of formula (III), may be chosen from, for example:

3-(m-aminophenoxy)propyltrimethoxysilane, of formula:

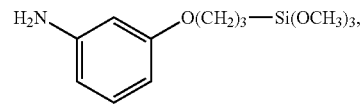

p-aminophenyltrimethoxysilane, of formula:

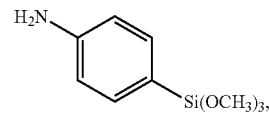

and

N-(2-aminoethylaminomethyl)phenethyltrimethoxysilane, of formula:

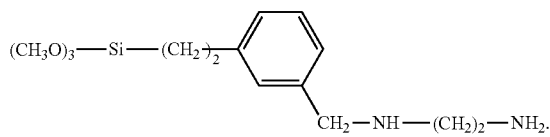

In another embodiment, the at least one alkoxysilane with at least one solubilizing functional group and at least one amino substituent may comprise at least one primary or secondary amine function.

In yet another embodiment, the at least one alkoxysilane with at least one solubilizing functional group and at least one amino substituent that can be used in the compositions disclosed herein, correspond to formula (I):

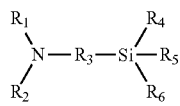

wherein:
$R_1$ and $R_2$, which may be identical or different, are independently chosen from a hydrogen atom and ethyl, propyl, and aminoethyl groups;
$R_3$ is chosen from ethyl, propyl and methylphenethyl groups;
$R_4$, $R_5$, and $R_6$, which may be identical or different, are independently chosen from methyl, methoxy, and ethoxy groups.

Non-limiting examples of the at least one alkoxysilane of formula (I) include, but are not limited to: 3-aminopropyl-triethoxysilane (APTES), 3-aminoethyltriethoxysilane (AETES), 3-aminopropylmethyldiethoxysilane, N-(2-aminoethyl)-3-aminopropyl-triethoxysilane and N-(2-aminoethylaminomethyl)-phenethyltrimethoxysilane of formula:

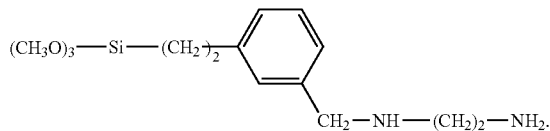

If present, the at least one alkoxysilane is in an amount of from about 0.05 to about 5 wt %, or from about 0.1 to about 4 wt %, or from about 0.15 to about 3 wt %, or from about 0.2 to about 2.5 wt %, of the booster composition, including all ranges and sub-ranges therebetween.

In one or more embodiments, the at least one alkoxysilane may be present in an amount of from about 0.05, 0.1, 0.15, 0.2, 0.25, 0.3, 0.35, 0.4, 0.45, 0.5 to about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 wt % of the booster composition.

Acid

The compositions according to the disclosed embodiments may optionally comprise at least one acid. In some embodiments, the acid may include mineral or organic acids, such as hydrochloric acid, orthophosphoric acid, sulfuric acid, sulfonic acids, and carboxylic acids. Examples of carboxylic acids include, for instance, acetic acid, tartaric acid, citric acid, and lactic acid. In one or more embodiments, the acid functions to neutralize the alkoxysilane. In some embodiments, the at least one acid is selected from the group consisting of lactic acid, phosphoric acid, orthophosphoric, citric acid, pyruvic acid, malic acid, hydrochloric acid, sulfuric acid, sulfonic acid, or mixtures thereof.

In one or more embodiments, the amount of acid depends on the degree to which neutralization of alkoxysilane is desired. In some embodiments, the acid is present in an amount to neutralize about 20, 30, 40, or 50, to about 60, 70, 80, 90, or 100% of the alkoxysilane. In some embodiments, the alkoxysilane may be further partially neutralized by acid, and then further neutralized by an anionic compound (for example, an anionic latex or non-latex polymer). Thus, the acid may be present in amounts ranging from about 0.01, 0.02, 0.03, 0.04, 0.05, 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, 10, 15, 20, or 25 to about 0.05, 0.1, 0.2, 0.3, 0.4, 0.5, 0.6, 0.7, 0.8, 0.9, 1.0, 1.5, 2, 2.5, 3, 3.5, 4, 4.5, 5, 6, 7, 8, 9, 10, 15, 20, 25, 30, 35, or 40 wt % by weight of the booster composition, including all ranges and sub-ranges therebetween.

Nonionic Latex Polymer

The booster compositions according to the disclosed embodiments may optionally comprise at least one nonionic latex polymer.

Suitable examples of the at least one nonionic latex polymer are selected from acrylates copolymer (DAITO-SOL 5000 AD, Kobo Products, Inc.), polyacrylate-2 crosspolymer (DAITOSOL 5000 SJ, Kobo Products, Inc.), styrene/acrylates copolymer (DAITOSOL 5000 STY, Kobo Products, Inc.), acrylates/ethylhexyl acrylate copolymer (DAITOSOL 4000 SJT, Kobo Products, Inc.), or mixtures thereof.

In an embodiment, the at least one nonionic latex polymer includes acrylates copolymer known as DAITOSOL 5000 AD, from Kobo Products, Inc.

If present, the at least one nonionic latex polymer is in an amount of from about 0.05 to about 5 wt %, or from about 0.1 to about 4 wt %, or from about 0.15 to about 3 wt %, or from about 0.2 to about 2.5 wt %, of the booster composition, including ranges and sub-ranges therebetween.

In one or more embodiments, the at least one nonionic latex polymer may be present in an amount of from about 0.05, 0.1, 0.15, 0.2, 0.25, 0.3, 0.35, 0.4, 0.45, 0.5 to about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 wt % of the booster composition, including ranges and sub-ranges therebetween.

c) Thickening Agent

Thickening agents may be referred to as "thickeners" or "viscosity modifying agents." Thickening agents are typically included to increase the viscosity of the compositions or to gellify the composition. Nonetheless, in some instances, certain thickening agents provide additional, surprising benefits, for example, styling and/or shaping benefits to hair, stability to the compositions, or spreadability and/or ease of application. Non-limiting examples of thickening agents include polyacrylate crosspolymers or crosslinked polyacrylate polymers, cationic acrylate copolymers, anionic acrylic or carboxylic acid polymers, carbomers, polyacrylamide polymers, polysaccharides such as cellulose and cellulose derivatives, guar and guar derivatives, starches, gums, vinylpyrrolidone homopolymers/copolymers, C8-24 hydroxyl substituted aliphatic acid, C8-24 conjugated aliphatic acid, sugar fatty esters, polyglyceryl esters, clays, silica, or mixtures thereof.

Particular types of thickening agents that may be useful according to various embodiments of the disclosure include the following.

a. Carboxylic acid or carboxylate based homopolymer or co-polymer, which can be linear or crosslinked:

These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid or carboxylate polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the cross-linking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULENTR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is aviable in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickeners useful herein are those selected from carbomers, acrylates/C10-C30 alkyl acrylate crosspolymers, polyacrylate crosspolymer-6, acrylamidopropyltrimonium chloride/acrylates copolymer, or mixtures thereof.

b. Polyquaternium Compounds:

Non-limiting examples include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc.

In some cases, preferred polyquaternium compounds include polyquaternium-10, polyquaternium-11, polyquaternium-67, or mixtures thereof.

c. Polysaccharides:

Non-limiting examples include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, hydroxypropyl guar, or mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the polysaccharide is preferably selected from hydroxyethylcellulose (HEC), hydroxypropylcellulose (HPC), hydroxypropyl guar, or mixtures thereof.

d. Polyvinylpyrrolidone (PVP) and copolymers:

Non-limiting examples include Polyvinylpyrrolidone (PVP), Polyvinylpyrrolidone(PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commercially available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

e. Sucrose esters:

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, or mixtures thereof.

f. Polyglyceryl esters:

Non-limiting polyglycerol esters of fatty acids (polyglyceryl esters) include those of the following formula:

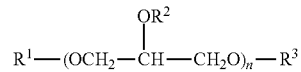

wherein:

n is from 2 to 20, or from 2 to 10, or from 2 to 5, or is 2, 3, 4, 5, 6, 7, 8, 9, or 10; and $R^1$, $R^2$, and $R^3$, which may be identical or different, are independently chosen from a fatty acid moiety or hydrogen, provided that at least one of $R^1$, $R^2$, and $R^3$ is a fatty acid moiety.

For instance, $R^1$, $R^2$ and $R^3$ may be saturated or unsaturated, straight or branched, and have a length of $C_1$-$C_{40}$, $C_1$-$C_{30}$, $C_1$-$C_{25}$, $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, or mixtures thereof.

g. $C_8$-$C_{24}$ hydroxyl substituted aliphatic acid, and $C_8$-$C_{24}$ conjugated aliphatic acid:

Non-limiting examples include conjugated linoleic acid, cis-parinaric acid, trans-7-octadecenoic acid, cis-5,8,11,14,17-eicosapentanoic acid, cis-4,7,10,13,16,19-docosahexenoic acid, columbinic acid, linolenelaidic acid, ricinolaidic acid, stearidonic acid, 2-hydroxystearic acid, alpha-linolenic acid, arachidonic acid, cis-11,14-eicosadienoic acid, linolelaidic acid, monopetroselinic acid, petroselinic acid, ricinoleic acid, trans-vaccenic acid, cis-11,14,17-eicosatrienoic acid, cis-5-eicosenoic acid, cis-8,11,14-eicosatrienoic acid, hexadecatrienoic acid, palmitoleic acid, petroselaidic acid, trans trans farnesol, cis-13,16-docosadienoic acid, cis-vaccenic acid, cis-11-eicosenoic acid, cis-13,16,19-docosatrienoic acid, cis-13-octadecenoic acid, cis-15-octadecanoic acid, cis-7,10,13,16 docosatetraenoic acid, elaidic acid, gamma-linolenic acid, geranic acid, geranyl geranoic acid, linoleic acid, oleic acid, pinolenic acid, trans-13-octadecenoic acid. More preferably, the aliphatic acid comprises 12-hydroxystearic acid, conjugated linoleic acid, or a mixture thereof.

h. Gums:

Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, cationic guar gum, etc.

In various exemplary embodiments, the at least one thickening agent of the present disclosure may be chosen from polysaccharides, in particular, cellulose derivatives, guar derivatives, and gum derivatives, such as cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, hydroxypropyl guar, xanthan gum, sclerotium gum, guar gum, cationic guar gum, or mixtures thereof. Furthermore, in some instances, the cellulose is preferably hydroxypropylcellulose (HPC) and/or hydroxyethylcellulose and/or hydroxypropyl guar.

The total amount of thickening agents can vary but is typically from about 0.1 to about 20 wt %, based on the total weight of the booster composition. In some instances, the total amount of thickening agents is about 0.1 to about 15 wt %, about 0.1 to about 10 wt %, about 0.3 to about 8 wt %, about 0.5 to about 6 wt %, about 0.5 to about 5 wt %, about 0.7 to about 3 wt %, or about 1 to about 3 wt %, based on the total weight of the booster composition, including all ranges and sub-ranges therebetween.

In one or more embodiments, the at least one thickening agent may be present in an amount of from about 0.1, 0.15, 0.2, 0.25, 0.3, 0.35, 0.4, 0.45, 0.5 to about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 wt % of the total booster composition, including all ranges and sub-ranges therebetween.

d) Cosmetically Acceptable Carrier

The booster compositions of the present disclosure contain a cosmetically acceptable carrier chosen from water, water-soluble solvents, or mixtures thereof.

Water

The booster compositions according to various embodiments of the disclosure may be aqueous. Water may be present in total amounts of about 95% or less, 90% or less, 85% or less, 80% or less, 75% or less, 70% or less, 65% or less, or 60% or less. For example, water may be present in amounts ranging from about 90% to about 40% by weight, about 80% to about 50% by weight, or about 90%, 80%, 70%, 60%, 50%, or 40% by weight, based on the total weight of the booster composition, including all ranges and sub-ranges therebetween. Additionally, water can be present in the booster compositions of the present disclosure in the amount of from about 50% to about 90 wt % by weight, from about 55% to about 85% by weight, or from about 60% to about 80% by weight, based on the total weight of the booster composition.

In other embodiments, water can be present in the booster compositions of the present disclosure in the amount of at least about 95%, 90%, 80%, 75%, 70%, 65%, 60%, 55%, 50%, 45%, or 40%, by weight, based on the total weight of the booster composition, including all ranges and sub-ranges therebetween.

Water-Soluble Solvents

The booster composition may include at least one water-soluble solvent. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90% in water under these conditions. Non-limiting examples of water-soluble organic solvents include, for example, glycerin, alcohols (for example, C1-C30, C1-C15, C1-C10, or C1-C4 alcohols), organic solvents, polyols, glycols, or mixtures thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanols (polyhydric alcohols such as glycols and polyols) such as glycerin, 1,2,6-hexanetriol, trimethylolpropane, ethylene glycol, propylene glycol, diethylene glycol, butylne glycol, hexylene glycol, triethylene glycol, tetraethylene glycol, pentaethylene glycol, dipropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, or mixtures thereof.

In some cases, the water-soluble solvent may be selected from the group consisting of one or more glycols, C1-4 alcohols, glycerin, or mixtures thereof, for example, isopropyl alcohol, glycerin, or a mixture thereof.

The total amount of the at least one water-soluble solvent may vary, but is typically about 0.1 to about 35 wt %, based on the total weight of the booster composition. The total amount of the at least one water-soluble solvent may be about 0.1 to about 30 wt %, about 0.1 to about 25 wt %, about 0.1 to about 20 wt %, about 0.1 to about 15 wt %, about 0.1 to about 10 wt %, about 0.1 to about 5 wt %, about 1 to about 35 wt %, about 1 to about 30 wt %, about 1 to about 25 wt %, about 1 to about 20 wt %, about 1 to about 15 wt %, about 1 to about 10 wt %, or about 1 to about 5 wt %, based on the total weight of the booster composition.

Surfactants

The hair treatment compositions according to the disclosure comprise at least one surfactant chosen from at least one anionic surfactant, at least one amphoteric surfactant, at least one cationic surfactant, at least one nonionic surfactant, or mixtures thereof.

Anionic Surfactants

When the hair treatment composition of the present disclosure is a shampoo or a cleansing composition, then the composition comprises at least one anionic surfactant. The anionic surfactants may be selected from non-sulfate anionic surfactants, sulfate anionic surfactants, their salts thereof, or mixtures thereof.

Non-Sulfate Anionic Surfactants

In some instances, the non-sulfate anionic surfactant(s) are the predominant type of surfactant in the surfactant system (i.e., there is a higher percentage of non-sulfate anionic surfactant(s) than any other single surfactant type in the cleansing composition). Moreover, in some instances, the total amount of non-sulfate anionic surfactants in the surfactant system is higher than the total amount of all other surfactant types in the surfactant system including amphoteric surfactants, nonionic surfactants, and any sulfate-based anionic surfactant that may be present. In other words, the phrase "all other surfactants" means any and all surfactants in the composition other than anionic surfactants.

When present, the total amount of non-sulfate anionic surfactants in the compositions can vary but typically ranges from about 4 to about 30 wt %, based on the total weight of the composition. In some cases, the total amount of non-sulfate anionic surfactants in the composition may be from about 4 to about 25 wt %, from about 5 to about 25 wt %, from about 5 to about 23 wt %, from about 6 to about 24 wt %, from about 6 to about 25 wt %, from about 7 to about 25 wt %, from about 8 to about 25 wt %, or from about 10 to about 23 wt %, based on the total weight of the composition.

In various embodiments, the total amount of non-sulfate anionic surfactants in the compositions, if present, is typically at about 6 wt %, 6.5 wt %, 7 wt %, 7.5 wt %, 8 wt %, 8.5 wt %, 8.8 wt %, 9 wt %, 9.5 wt %, 10 wt %, 10.5 wt %, 11 wt %, 11.4 wt %, 12 wt %, 12.5 wt %, 13 wt %, 13.5 wt %, 14 wt %, 14.5 wt %, 15 wt %, 15.5 wt %, 16 wt %, 16.5 wt %, 17 wt %, 17.5 wt %, 18 wt %, 18.5 wt %, 19 wt %, 19.5 wt %, 20 wt %, 20.5 wt %, 21 wt %, 21.5 wt %, 22 wt %, 22.5 wt %, 23 wt %, 23.5 wt %, 24 wt %, 24.5 wt %, or 25 wt %, based on the total weight of the composition.

Useful non-sulfate anionic surfactants include, but are not limited to, alkyl sulfonates, alkyl sulfosuccinates, alkyl sulfoacetates, acyl isethionates, alkoxylated monoacids, acyl amino acids such as acyl taurates, acyl glycinates, acyl glutamates, acyl sarcosinates, salts thereof, or mixtures thereof. Non-limiting examples of useful non-sulfate anionic surfactants are provided below.

Acyl Isethionates

Non-limiting examples of useful acyl isethionates and their salts include those of formula (I) and (II):

$$RCOOCHR^1CHR^2X^-M^+ \quad (I)$$

$$RCOOCHR^1CHR^2X^-Na^+ \quad (II)$$

wherein:
R, $R^1$, and $R^2$ are each independently chosen from H or an alkyl chain having 1-24 carbon atoms, said chain being saturated or unsaturated, linear or branched;
X is $COO^-$ or $SO_3^-$; and
M is any suitable cation.

Although the cation may be chosen from any suitable cation as in formula (I), including, for example, alkali metal ion such as sodium or potassium, ammonium ions, or alkanolammonium ions such as monoethanolammonium or triethanolammonium ions, sodium is a preferred cation, as in formula (II). In various embodiments, RCO-represents the coconut acid moiety. Non-limiting examples of acyl isethionates include sodium cocoyl isethionate, sodium lauroyl isethionate, sodium lauroyl methyl isethionate, and sodium cocoyl methyl isethionate.

Acyl Sarcosinates

Non-limiting examples of acyl sarcosinates and their salts include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate.

In some embodiments, the total amount of acyl sarcosinates in the hair treatment composition, if present, is from about 0.5 to about 10 wt %, based on the total weight of the composition. In some instance, the total amount of acyl sarcosinates in the composition is from about 0.5 to about 10 wt %, about 1 to about 8 wt %, about 1.5 to about 7 wt %, about 1.75 to about 6 wt %, 2 to about 5 wt %, about 2 to about 4 wt %, about 2.5 to about 4 wt %, about 2.5 to about 3.5 wt %, or about 2.7 to about 3 wt %, based on the total weight of the composition, including all ranges and subranges therebetween.

Alkyl Sulfonates

Useful alkyl sulfonates and their salts include alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenvlalkanesulfonates, alpha-olefinsulfonates, olefin sulfonates, alkene sulfonates, hydroxyalkanesulfonates and disulfonates, secondary alkanesulfonates, paraffin sulfonates, ester sulfonates, sulfonated fatty acid glycerol esters, and alpha-sulfo fatty acid methyl esters including methyl ester sulfonate.

In some instances, an alkyl sulfonate of formula (III) is particularly useful:

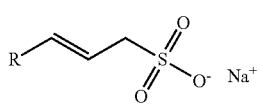
(III)

wherein R is selected from H or alkyl chain that has 1-24 carbon atoms, preferably 6-24 carbon atoms, more preferably, 8 to 20 carbon atoms, said chain being saturated or unsaturated, linear or branched, substituted or unsubstituted. Sodium is shown as the cation in the above formula (III) but the cation may be an alkali metal ion such as sodium or potassium, ammonium ions, or alkanolammonium ions such as monoethanolammonium or triethanolammonium ions.

In some instances, the alkyl sulfonate(s) are selected from $C_8$-$C_{16}$ alkyl benzene sulfonates, $C_{10}$-$C_{20}$ paraffin sulfonates, $C_{10}$-$C_{24}$ olefin sulfonates, salts thereof, or mixtures thereof. $C_{10}$-$C_{24}$ olefin sulfonates are particularly preferred. A non-limiting but particularly useful example of a $C_{10}$-$C_{24}$ olefin sulfonate that can be used in the instant compositions is sodium $C_{14-16}$ olefin sulfonate.

Alkyl Sulfosuccinates

Non-limiting examples of useful alkyl sulfosuccinates and their salts include those of formula (IV):

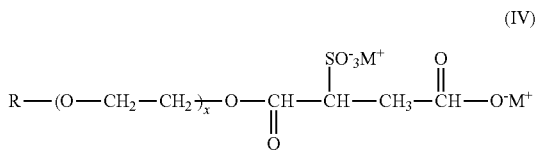
(IV)

wherein:
R is a straight or branched chain alkyl or alkenyl group having 10 to 22 carbon atoms, preferably 10 to 20 carbon atoms;
x is a number that represents the average degree of ethoxylation, and can range from 0 to about 5, preferably from 0 to about 4, and most preferably from about 2 to about 3.5; and
M, which can be the same or different, is chosen from any suitable monovalent cation.

Preferred cations are alkali metal ions such as sodium or potassium, ammonium ions, or alkanolammonium ions such as monoethanolammonium or triethanolammonium ions.

Non-limiting examples of alkyl sulfosuccinates salts include disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, or mixtures thereof. In some instances, disodium laureth sulfosuccinate is particularly preferred.

Alkyl Sulfoacetates

Non-limiting examples of alkyl sulfoacetates and their salts include, for example, alkyl sulfoacetates such as C4-C18 fatty alcohol sulfoacetates and/or salts thereof. A particularly preferred sulfoacetate salt is sodium lauryl sulfoacetate. Useful cations for the salts include alkali metal ions such as sodium or potassium, ammonium ions, or alkanolammonium ions such as monoethanolammonium or triethanolammonium ions.

Alkoxylated Monoacids

Non-limiting examples of alkoxylated monoacids include compounds corresponding to formula (V):

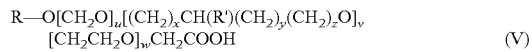
(V)

wherein:
R is a hydrocarbon radical containing from about 6 to about 40 carbon atoms;
R' represents hydrogen or alkyl;
u, v, and w, which may be identical or different, independently represent numbers from 0 to 60;
x, y, and z, which may be identical or different, independently represent numbers from 0 to 13; and
the sum of x+y+z>0.

Compounds corresponding to formula (V) can be obtained by alkoxylation of alcohols R—OH with ethylene oxide as the sole alkoxide or with several alkoxides and subsequent oxidation. The numbers u, v, and w each represent the degree of alkoxylation. Whereas, on a molecular level, the numbers u, v, and w and the total degree of alkoxylation can only be integers, including zero, on a macroscopic level they are mean values in the form of broken numbers.

In formula (V), R is linear or branched, acyclic or cyclic, saturated or unsaturated, aliphatic or aromatic, substituted or unsubstituted. Typically, R is a linear or branched, acyclic C6-C40 alkyl or alkenyl group or a C1-C40 alkyl phenyl group, more typically a C8-C22 alkyl or alkenyl group, or a C4-C18 alkyl phenyl group, and even more typically a C12-C18 alkyl group or alkenyl group or a C6-C16 alkyl phenyl group. Further, u, v, w, independently of one another, are typically chosen from a number ranging from 2 to 20, more typically a number ranging from 3 to 17, and most typically a number ranging from 5 to 15. Further still, x, y, z, independently of one another, are typically chosen from a number ranging from 0 to 13, more typically a number ranging from 1 to 10, and most typically a number ranging from 2 to 8.

Suitable alkoxylated monoacids include, but are not limited to: Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid, or mixtures thereof. In some cases, preferred ethoxylated acids include Oleth-10 Carboxylic Acid, Laureth-5 Carboxylic Acid, Laureth-11 Carboxylic Acid, or mixtures thereof.

Acyl Amino Acids

Acyl amino acids that may be used include, but are not limited to, amino acid surfactants based on alanine, arginine, aspartic acid, glutamic acid, glycine, isoleucine, leucine, lysine, phenylalanine, serine, tyrosine, valine, sarcosine, threonine, and taurine. The most common cation associated with the acyl amino acid can be sodium or potassium. Alternatively, the cation can be an organic salt such as triethanolamine (TEA) or a metal salt.

Non-limiting examples of useful acyl amino acids include those of formula (VI):

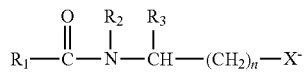
(VI)

wherein:
$R^1$, $R^2$, and $R^3$ are each independently selected from H or an alkyl chain having 1-24 carbon atoms, said chain being saturated or unsaturated, linear or branched, substituted or unsubstituted;
n ranges from 0 to 30; and
X is $COO^-$ or $SO_3^-$.

In various embodiments, RCO— represents the coconut acid moiety. A non-limiting example is sodium cocoyl glycinate.

Acyl Taurates

Non-limiting examples of acyl taurates include those of formula (VII):

$$RCO-NR^1CHR^2CHR^3SO_3Na \quad (VII)$$

wherein R, $R^1$, $R^2$, and $R^3$ are each independently selected from H or an alkyl chain having from 1-24 carbon atoms, such as from 6-20 carbon atoms, or from 8-16 carbon atoms, said chain being saturated or unsaturated, linear or branched, substituted or unsubstituted.

In various embodiments, RCO— represents the coconut acid moiety. Non-limiting examples of acyl taurate salts include sodium cocoyl taurate and sodium methyl cocoyl taurate.

Acyl Glycinates

Non-limiting examples of useful acyl glycinates include those of formula (VIII):

(VIII)

wherein R is an alkyl chain of 8 to 16 carbon atoms. Sodium is shown as the cation in the above formula (VIII), but the cation may be any alkali metal ion such as sodium or potassium, ammonium ions, or alkanolammonium ions such as monoethanolammonium or triethanolammonium ions.

Non-limiting examples of acyl glycinates include sodium cocoyl glycinate, sodium lauroyl glycinate, sodium myristoyl glycinate, potassium lauroyl glycinate, and potassium cocoyl glycinate, and in particular sodium cocoyl glycinate.

Acyl Glutamates

Non-limiting examples of useful acyl glutamates include those of formula (IX):

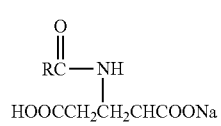
(IX)

wherein R is an alkyl chain of 8 to 16 carbon atoms. Sodium is shown as the cation in the above formula (IX) but the cation may be any alkali metal ion such as sodium or potassium, ammonium ions, or alkanolammonium ions such as monoethanolammonium or triethanolammonium ions.

Non-limiting examples of acyl glutamates include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate. In some cases, sodium stearoyl glutamate is particularly preferred.

In an embodiment, the non-sulfate anionic surfactants of the compositions of the present disclosure may be selected from one or more acyl isethionates, their salts, or mixtures thereof.

In an embodiment, the one or more acyl isethionates, their salts, or mixtures thereof are selected from sodium cocoyl isethionate, sodium lauroyl methyl isethionate, sodium cocoyl methyl isethionate, sodium lauroyl isethionate, or mixtures thereof.

In an embodiment, the non-sulfate anionic surfactants of the compositions of the present disclosure are selected from one or more acyl sarcosinates, their salts, or mixtures thereof.

In an embodiment, the one or more acyl sarcosinates, their salts, or mixtures thereof are selected from sodium cocoyl sarcosinate, sodium lauroyl sarcosinate, potassium lauroyl sarcosinate, potassium cocoyl sarcosinate, sodium myristoyl sarcosinate, sodium oleoyl sarcosinate, sodium palmitoyl sarcosinate, ammonium lauroyl sarcosinate, or mixtures thereof.

In some cases, a plurality of non-sulfate anionic surfactants may be preferred. For example, two or more, such as three or more non-sulfate anionic surfactants may be selected from acyl isethionates, acyl sarcosinates, alkyl sulfonates, alkyl sulfosuccinates, alkyl sulfoacetates, alkoxylated monoacids, and acyl amino acids such as acyl taurates, acyl glycinates, acyl glutamates, salts thereof, or mixtures thereof.

One preferred embodiment of the compositions of the present disclosure includes a combination of non-sulfate anionic surfactants chosen from one or more acyl isethionates (and/or salts thereof) and one or more acyl sarcosinates (and/or salts thereof).

One exemplary embodiment of the compositions of the present disclosure includes a combination of non-sulfate anionic surfactants chosen from one or more acyl isethionates (and/or salts thereof), one or more acyl sarcosinates (and/or salts thereof), and one or more non-sulfate anionic surfactants and/or salts thereof selected from alkyl sulfonates, alkyl sulfosuccinates, alkyl sulfoacetates, alkoxylated monoacids, acyl amino acids such as acyl taurates, acyl glycinates, acyl glutamates, or mixtures thereof.

Sulfate Anionic Surfactants

Optionally, anionic surfactants may be chosen from sulfate anionic surfactants. Such sulfate anionic surfactants may be chosen from, for example, alkyl sulfates, alkyl ether sulfates, and/or salts thereof.

By way of example, alkyl sulfates may include C8-18 alkyl sulfates, more preferably C12-18 alkyl sulfates, such as in the form of a salt with a solubilizing cation such as sodium, potassium, ammonium, or substituted ammonium. Examples include but are not limited to sodium lauryl sulfate (SLS) and sodium dodecyl sulfate (SDS).

As a further example, alkyl ether sulfates may include those having the formula:

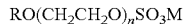

wherein:

R is an alkyl or alkenyl having from 8 to 18 (preferably 12 to 18) carbon atoms;

n is a number having an average value of greater than at least 0.5, preferably between 1 and 3, more preferably between 2 and 3; and M is a solubilizing cation such as sodium, potassium, ammonium or substituted ammonium.

An example of a useful alkyl ether sulfate is sodium lauryl ether sulfate (SLES).

In some instances, useful alkyl sulfate salts and alkyl ether sulfate salts include those having the formulas (X and XI):

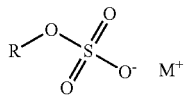

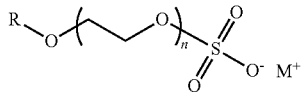

wherein:

R is an alkyl chain having from 6 to 24 carbon atoms, preferably 8 to 18 carbon atoms, and more preferably 12 to 18 carbon atoms;

M is a solubilizing cation such as alkali metal ions such as sodium or potassium, ammonium ions, or alkanolammonium ions such as monoethanolammonium or triethanolammonium ions; and n is an integer from 0 to 3.

If present, the total amount of alkyl sulfates, alkyl ether sulfates, and/or salts thereof in the compositions can vary, but typically ranges from about 5 to about 50 wt %, based on the total weight of the composition. In some cases, the total amount of alkyl sulfates, alkyl ether sulfates, and/or salts thereof in the composition may be from about 5 to about 45 wt %, from about 5 to about 30 wt %, from about 5 to about 25 wt %, from about 5 to about 20 wt %, from about 5 to about 15 wt %, from about 10 to about 45 wt %, from about 10 to about 50 wt %, from about 10 to about 40 wt %, from about 10 to about 35 wt %, from about 10 to about 30 wt %, about 10 to about 25 wt %, about 10 to about 20 wt %, from about 12 to about 50 wt %, from about 12 to about 45 wt %, from about 12 to about 40 wt %, from about 12 to about 35 wt %, or from about 13 to about 30 wt %, or from about 14 to about 25 wt %, based on the total weight of the composition, including ranges and sub-ranges therebetween.

In some instances, the hair treatment compositions according to the disclosure do not require silicones and/or sulfate-based anionic surfactants. Thus, any one or more (or all) of these may optionally be excluded from the compositions. In other words, the compositions may be free or essentially free of silicones and/or sulfate-based anionic surfactants. Nonetheless, in some instances, one or more silicones and/or one or more sulfate-based surfactants may optionally be included in at least certain embodiments of the compositions.

Amphoteric Surfactants

In certain embodiments when the hair treatment composition of the present disclosure is a shampoo or a cleansing composition that contains at least one anionic surfactant, then the composition may further comprise at least one amphoteric surfactant. The amphoteric surfactants may, for example, be selected from betaines, alkyl sultaines, alkyl amphoacetates and alkyl amphodiacetates, alkyl amphopropionates, salts thereof, or mixtures thereof.

In various embodiments, the betaines are selected from alkyl betaines, alkyl amidopropyl betaines, alkyl sulfobetaines (sultaines), or mixtures thereof.

In an embodiment, the amphoteric surfactants are selected from cocamidopropyl betaine, coco-betaine, or mixtures thereof.

If present, the total amount of amphoteric surfactant(s) in the compositions may vary, but is typically from about 0.05 to about 10 wt %, based on the total weight of the composition. In some instance, the total amount of amphoteric surfactant(s) in the composition is from about 0.05 to about 8 wt %, from about 0.1 to about 7 wt %, from about 0.1 to about 6 wt %, from about 0.15 to about 6 wt %, from about 0.15 to about 5 wt %, from about 0.15 to about 4 wt %, from about 0.15 to about 3 wt %, or from about 0.2 to about 2.5 wt %, based on the total weight of the composition, including ranges and sub-ranges therebetween.

Betaines

Exemplary useful betaines include, but are not limited to, those of the following formulae (XIIa-XIId):

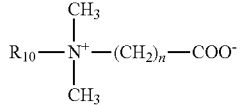

(XIIa)

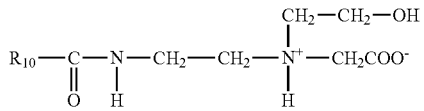

(XIIb)

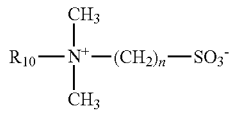

(XIIc)

-continued

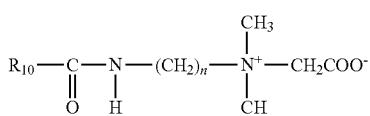 (XIId)

wherein:

$R_{10}$ is an alkyl group having from 8-18 carbon atoms; and n is an integer from 1 to 3.

Particularly useful betaines include, for example, cocobetaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, or mixtures thereof. Particularly preferred betaines include coco-betaine and cocamidopropyl betaine.

Alkyl Sultaines

Non-limiting examples of alkyl sultaines include hydroxyl sultaines of formula (XIII):

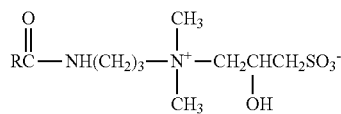 (XIII)

wherein R is an alkyl group having 8-18 carbon atoms.

More specific examples include, but are not limited to cocamidopropyl hydroxysultaine, lauryl hydroxysultaine, or mixtures thereof.

Alkyl Amphoacetates and Alkyl Amphodiacetates

Useful alkyl amphoacetates and alkyl amphodiacetates include those of formulae (XIV) and (XV):

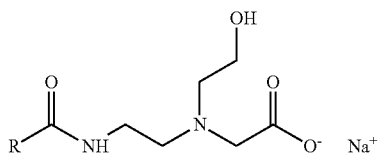 (XIV)

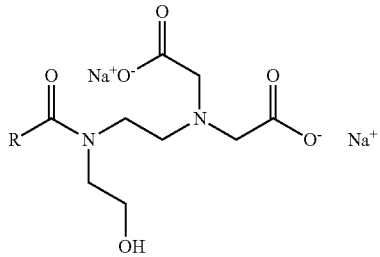 (XV)

wherein R is an alkyl group having 8-18 carbon atoms. Although sodium is shown as the cation in the above formulae, the cation may be any alkali metal ion, such as sodium or potassium, ammonium ions, or alkanolammonium ions such as monoethanolammonium or triethanolammonium ions. A non-limiting example is sodium lauroamphoacetate.

Alkyl Amphopropionates

Exemplary and non-limiting examples of useful alkyl amphopropionates include cocoamphopropionate, caprylamphopropionate, cornamphopropionate, caproamphopropionate, oleoamphopropionate, isostearoamphopropionate, stearoamphopropionate, lauroamphopropionate, salts thereof, or mixtures thereof.

Cationic Surfactants

When the hair treatment composition of the present disclosure is a conditioner or rinse-off or leave-in mask composition, then typically, the composition comprises at least one cationic surfactant. The term "cationic surfactant" means a surfactant that may be positively charged when it is contained in the compositions according to the disclosure. This surfactant may bear one or more positive permanent charges or may contain one or more functional groups that are cationizable in the composition according to the disclosure. Suitable cationic surfactants include a quaternary ammonium compound that is a mono- or double-chain quaternary ammonium compound, wherein each chain independently has from about 14 to about 30 carbon atoms; and the quaternary ammonium compound has a cosmetically acceptable counterion selected from chloride, bromide, and methosulfate.

Other suitable cationic surfactants are mono-long chain alkyl amines, including, for example, alkyl amidoamines.

Non-limiting examples of alkyl amines include brassicamidopropyl dimethylamine, stearyl dimethyl amine, and stearamidopropyl dimethylamine.

Useful are tertiary amido amines having an alkyl group of from about 12 to about 22 carbons. Exemplary tertiary amido amines include: brassicamidopropyl dimethylamine, stearamidopropyldimethylamine, stearamidopropyldiethylamine, stearamidoethyldiethylamine, stearamidoethyldimethylamine, palmitamidopropyl-dimethylamine, palmitamidopropyldiethylamine, palmitamidoethyldiethylamine, palmitamidoethyldimethylamine, behenamidopropyldimethylamine, behenamido-propyldiethylamine, behenamidoethyldiethylamine, behenamidoethyldimethylamine, arachidamidopropyldimethylamine, arachidamidopropyldiethylamine, arachidam ido-ethyldiethylamine, arachidamidoethyldimethylamine, and diethylaminoethyl-stearamide.

These amines may be used in combination with acids such as l-glutamic acid, lactic acid, hydrochloric acid, malic acid, succinic acid, acetic acid, fumaric acid, tartaric acid, citric acid, l-glutamic hydrochloride, maleic acid, or mixtures thereof; more preferably l-glutamic acid, lactic acid, and citric acid.

If present, the total amount of cationic surfactant(s) in the hair treatment compositions may vary, but is typically present in an amount ranging from about 0.01 to about 10 wt %, based on the total weight of the composition. In some instance, the total amount of cationic surfactant(s) in the composition ranges from about 0.05 to about 9 wt %, from about 0.05 to about 8 wt %, from about 0.1 to about 8 wt %, from about 0.15 to about 6 wt %, from about 0.2 to about 6 wt %, from about 0.25 to about 6 wt %, from about 0.25 to about 5 wt %, from about 0.3 to about 5 wt %, from about 0.3 to about 4 wt %, or from about 0.4 to about 3 wt %, based on the total weight of the composition, including all ranges and sub-ranges therebetween.

In various embodiments, the at least one cationic surfactant may be selected from cetrimonium chloride, cetrimonium methosulfate, stearimonium chloride, behentrimonium chloride, behentrimonium methosulfate, behenamidopropyltrimonium methosulfate, stearamidopropyltrimonium chloride, arachidtrimonium chloride, distearyldimonium chloride, cetyltrimethylammonium chloride, cetyltrimethylammonium bromide, dipalmitoylethyl hydroxyethylmonium methosulfate, dicetyldimonium chloride (Varisoft 432 PPG), tricetylmonium chloride, oleamidopropyl dimethylamine, linoleamidopropyl dimethylamine, isostear-amidopropyl dimethylamine, oleyl hydroxyethyl imidazoline, stearamidopropyldimethylamine, behenamidopropyldimethylamine, behenamido-propyldiethylamine, behenamidoethyldiethylamine, behenamidoethyldimethylamine, arachidamidopropyldimethylamine, arachidamidopropyidiethylamine, arachidam ido-ethyldiethylamine, arachidamidoethyldimethylamine, brassicam idopropyldimethyl-amine, or mixtures thereof.

According to some embodiments of the disclosure, the booster compositions may also comprise at least one cationic surfactant. The aforementioned types and amounts of cationic surfactants may therefore also be chosen for use in, and relative to the weight of, the booster compositions. By way of non-limiting example, the booster composition may comprise at least one cationic surfactant, present in an amount ranging from about 0.1 to about 5 wt %, from about 0.15 to about 4 wt %, from about 0.2 to about 3 wt %, from about 0.25 to about 2 wt %, or from about 0.25 to about 1 wt %, by weight of the booster composition.

Nonionic Surfactants

The hair treatment compositions of the present disclosure may include at least one nonionic surfactant.

The total amount of nonionic surfactant(s), if present, can vary, but may be in an amount ranging from about 0.01 to about 25 wt %, based on the total weight of the composition. In some instance, the total amount of nonionic surfactant(s) in the composition ranges from about 0.01 to about 20 wt %, from about 0.01 to about 15 wt %, about 0.01 to about 10 wt %, from about 0.01 to about 5 wt %, from about 0.1 to about 25 wt %, from about 0.1 to about 20 wt %, from about 0.1 to about 15 wt %, or from about 0.1 to about 10 wt %, or about 0.1 to about 8 wt %, based on the total weight of the composition, including all ranges and sub-ranges therebetween.

The nonionic surfactant(s) can be, for example, selected from alkyl polyglucosides, fatty amide, fatty alcohols, alpha-diols, alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides, or mixtures thereof.

Such nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a C8-C24, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a C8-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; or mixtures thereof.

Examples of ethoxylated fatty esters that may be mentioned include the adducts of ethylene oxide with esters of lauric acid, palmitic acid, stearic acid or behenic acid, or mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palm itate (as the CTFA names: PEG-9 palm itate to PEG-50 palmitate); PEG-9 to PEG-50 stearate (as the CTFA names: PEG-9 stearate to PEG-50 stearate); PEG-9 to PEG-50 palm itostearate; PEG-9 to PEG-50 behenate (as the CTFA names: PEG-9 behenate to PEG-50 behenate); polyethylene glycol 100 EO monostearate (CTFA name: PEG-100 stearate); or mixtures thereof.

As glyceryl esters of fatty acids, glyceryl stearate (glyceryl mono-, di- and/or tristearate) (CTFA name: glyceryl stearate) or glyceryl ricinoleate or mixtures thereof can in particular be cited.

As glyceryl esters of C8-C24 alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1N by Goldschmidt (CTFA name: glyceryl stearate SE), can also be used.

Useful alkyl polyglucosides include those having the following formula (XVI):

$$R^1-O-(R^2O)_n-Z_{(x)} \quad\quad (XVI)$$

wherein:

$R^1$ is an alkyl group having 8-18 carbon atoms;

$R^2$ is an ethylene or propylene group;

Z is a saccharide group with 5-6 carbon atoms;

n is an integer ranging from 0 to 10; and x is an integer ranging from 1 to 5.

Useful alkylpolyglucosides include lauryl glucoside, octyl glucoside, decyl glucoside, coco glucoside, caprylyl/capryl glucoside, sodium lauryl glucose carboxylate, or mixtures thereof. Typically, the alkyl polyglucoside compound is selected from the group consisting of lauryl glucoside, decyl glucoside, coco glucoside, or mixtures thereof. In some instances, decyl glucoside is particularly preferred.

The fatty alcohols that may be used in the composition of the disclosure include, but are not limited to, non-alkoxylated, saturated or unsaturated, linear or branched, and have from 6 to 60 carbon atoms, such as from 8 to 30 carbon atoms.

The fatty alcohols of the present disclosure are chosen from solid and liquid fatty alcohols.

The saturated liquid fatty alcohols can be branched. They can optionally comprise, in their structure, at least one aromatic or non-aromatic ring. They can be acyclic.

The unsaturated liquid fatty alcohols exhibit, in their structure, at least one double or triple bond, and preferably one or more double bonds. When several double bonds are present, there are preferably 2 or 3 of them and they can be conjugated or unconjugated. These unsaturated fatty alcohols can be linear or branched. They can optionally comprise, in their structure, at least one aromatic or non-aromatic ring. They can be acyclic. Among the liquid unsaturated fatty alcohols, oleyl alcohol, linoleyl alcohol, linolenyl alcohol and undecylenyl alcohol may be mentioned.

Liquid fatty alcohols may be selected, for example, from octyldodecanol, 2-butyloctanol, 2-hexyldecanol, 2-undecylpentadecanol, oleyl alcohol or linoleyl alcohol, isostearyl alcohol, or mixtures thereof.

Solid fatty alcohols may be crystalline, amorphous, or pasty. The solid fatty alcohols of the present invention are solid at room temperature (25° C.) and at atmospheric pressure (1 atm), and are insoluble in water (i.e. they have a solubility in water of less than 1% by weight and preferably less than 0.5% by weight, at 25° C. and 1 atm) and are soluble, under the same temperature and pressure conditions, in at least one organic solvent (for example ethanol, chloroform, benzene, or liquid petroleum jelly) to at least 1% by weight.

In one embodiment, the solid fatty alcohols preferably have a melting point of greater than or equal to 28° C. and have a viscosity, at a temperature of 40° C. and at a shear rate of 1 s$^{-1}$, of greater than or equal to 1 Pa·s.

In an embodiment, the melting point of the fatty alcohols ranges from 30° C. to 250° C., such as from 32° C. to 150° C., or from 35° C. to 150° C.

The melting points may be measured by DSC or on a Kofler bench. The melting point may be measured by differential calorimetric analysis (DSC) with a temperature rise of 10° C. per minute. The melting point is then the temperature corresponding to the top of the melting endotherm peak obtained during the measurement.

The viscosity measurements may be taken at a temperature of about 40° C. using an RS600 rheometer from Thermoelectron.

The solid fatty alcohols of the present invention are chosen from saturated or unsaturated, linear or branched, preferably linear and saturated, (mono) alcohols comprising from 6 to 60 carbon atoms, such as from 10 to 50 carbon atoms, or from 12 to 24 carbon atoms.

The solid fatty alcohols preferably have the structure of the following formula:

in which R especially denotes a C6-C60, for example, C8-C60, preferably C10-050 or even C12-C30 alkyl group, R possibly being substituted with one or more hydroxyl groups, R possibly being branched. The solid fatty alcohols of the invention may be non-oxyalkylenated and/or non-glycerolated. These fatty alcohols may be constituents of animal or plant waxes.

The solid fatty alcohol may represent a mixture of fatty alcohols, which means that several species of fatty alcohol may coexist, in the form of a mixture, in a commercial product. One example of such a commercial product is cetearyl alcohol, a mixture of cetyl alcohol and stearyl alcohol, commercially available under the trade name of LANETTE 0 OR from the company BASF. Cetyl alcohol may also be commercially available under the tradename of LANETTE 16 from the company BASF.

In an embodiment, the solid fatty alcohols of the present invention may be chosen from myristyl alcohol, cetyl alcohol, stearyl alcohol, cetearyl alcohol, or mixtures thereof, octyldodecanol, 2-butyloctanol, 2-hexyldecanol, 2-undecylpentadecanol, oleic alcohol, linoleic alcohol, behenyl alcohol, or mixtures thereof.

Other suitable examples of the solid fatty alcohol of the present invention include branched solid fatty alcohols chosen from 2-dodecylhexadecanol, 2-tetradecyl-1-octadecanol, 2-tetradecyl-1-eicosanol, 2-hexadecyl-1-octadecanol, and 2-hexadecyl-1-eicosanol, or mixtures thereof.

In an embodiment of the present invention, the fatty alcohol is chosen from non-alkoxylated, saturated or unsaturated, linear or branched fatty alcohol having from 6 to 60 carbon atoms is chosen from cetyl alcohol, stearyl alcohol, cetearyl alcohol (mixture of cetyl alcohol and stearyl alcohol), octyldodecanol, 2-butyloctanol, 2-hexyldecanol, 2-undecylpentadecanol, oleic alcohol, linoleic alcohol, behenyl alcohol, 2-dodecylhexadecanol, 2-tetradecyl-1-octadecanol, 2-tetradecyl-1-eicosanol, 2-hexadecyl-1-octadecanol and 2-hexadecyl-1-eicosanol, octyldodecanol, 2-butyloctanol, 2-hexyldecanol, 2-undecylpentadecanol, oleyl alcohol or linoleyl alcohol, isostearyl alcohol, or mixtures thereof.

In an embodiment, the at least one nonionic surfactant is selected from alkyl polyglucosides, fatty alcohols, alkoxylated fatty alcohols, sorbitan derivatives, glyceryl esters, or mixtures thereof.

In an embodiment, when the composition of the present disclosure is a conditioner or rinse-off or leave-in mask composition, the composition comprises at least one nonionic surfactant selected from fatty alcohols.

In an embodiment of the present invention, the fatty alcohol is chosen from cetyl alcohol.

In an embodiment of the present invention, the fatty alcohol is chosen from cetearyl alcohol.

In an embodiment of the present invention, the fatty alcohol comprises cetyl alcohol and cetearyl alcohol.

In an embodiment of the present invention, the fatty alcohol comprises cetyl alcohol and stearyl alcohol.

In an embodiment of the present invention, the fatty alcohol is chosen from cetyl alcohol, stearyl alcohol, cetearyl alcohol, or mixtures thereof.

In an embodiment, the fatty alcohols of the present invention are chosen from liquid fatty alcohol, solid fatty alcohols, or mixtures thereof.

The fatty alcohol(s) may be present in the composition of the present disclosure in an amount ranging from about 0.1 to about 20 wt % by weight, such as from about 0.75 to about 15 wt % by weight, from about 1% to about 12 wt % by weight, from about 1 to about 10 wt % by weight, from about 1.5 to about 10 wt %, from about 1.5 to about 9 wt %, or from about 2 to about 8 wt. %, based on the total weight of the composition, including all ranges and sub-ranges therebetween.

In various embodiments, the total amount of the fatty alcohol(s), if present, is typically at about 0.1 wt %, 0.2 wt %, 0.3 wt %, 0.4 wt %, 0.5 wt %, 0.6 wt %, 0.7 wt %, 0.75 wt %, 0.8 wt %, 0.9 wt %, 1 wt %, 1.25 wt %, 1.5 wt %, 1.7 wt %, 1.75 wt %, 2 wt %, 2.25 wt %, 2.5 wt %, 2.75 wt %, 3 wt %, 3.5 wt %, 4 wt %, 4.5 wt %, 5 wt %, 5.5 wt %, 6 wt %, 6.5 wt %, 7 wt. %, 7.5 wt %, or 8 wt %, based on the total weight of the hair treatment composition.

According to some embodiments of the disclosure, the booster compositions may also comprise at least one nonionic surfactant. The aforementioned types and amounts of nonionic surfactants may therefore also be chosen for use in, and relative to the weight of, the booster compositions. By way of non-limiting example, the booster composition may comprise at least one nonionic surfactant, present in an amount ranging from about 0.1 to about 5 wt %, from about 0.1 to about 4 wt %, from about 0.15 to about 3 wt %, from about 0.15 to about 2 wt %, from about 0.2 to about 1 wt %, or from about 0.2 to about 0.5 wt %, by weight of the booster composition.

Fatty Compounds

The hair treatment and/or booster compositions according to the disclosure may optionally comprise one or more fatty compounds. Fatty compounds that may be present include "non-silicone fatty compounds," i.e., fatty compounds that do not containing any silicon (Si) atoms. Non-limiting examples of non-silicone fatty compounds include oils, mineral oil, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, or mixtures thereof. Non-limiting examples of the fatty acids, fatty alcohol derivatives, and fatty acid derivatives are found in International Cosmetic Ingredient Dictionary, Sixteenth Edition, 2016, which is incorporated by reference herein in its entirety.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, or mixtures thereof. In some cases, the fatty acids are selected from the group consisting of palmitic acid, stearic acid, or mixtures thereof.

Fatty alcohol derivatives include alkyl ethers of fatty alcohols, alkoxylated fatty alcohols, alkyl ethers of alkoxylated fatty alcohols, esters of fatty alcohols or mixtures thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcocohl, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; or mixtures thereof.

Non-limiting examples of polyglycerol esters of fatty acids include those of the following formula (XVII):

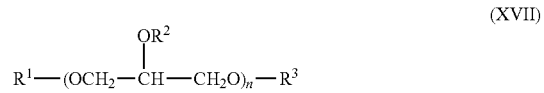

(XVII)

wherein:

the average value of n is about 3; and $R^1$, $R^2$, and $R^3$, which may be identical or different, are independently chosen from a fatty acid moiety or hydrogen, provided that at least one of $R^1$, $R^2$, and $R^3$ is a fatty acid moiety.

For instance, $R^1$, $R^2$ and $R^3$ may be saturated or unsaturated, straight or branched, and have a length of $C_1$-$C_{40}$, $C_1$-$C_{30}$, $C_1$-$C_{25}$, $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, or mixtures thereof.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, or mixtures thereof. Nonlimiting examples of fatty acid derivatives include ricinoleic acid, glycerol monostearate, 12-hydroxy stearic acid, ethyl stearate, cetyl stearate, cetyl palm itate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, or mixtures thereof. Preferred for use herein are glycerol monostearate, 12-hydroxy stearic acid, or mixtures thereof.

In some cases, the one or more fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, or 50° C. or higher. The high melting point fatty compound may be selected from fatty acids, fatty alcohol derivatives, fatty acid derivatives, or mixtures thereof. Nonlimiting examples of the high melting point compounds are found in the International Cosmetic Ingredient Dictionary, Sixteenth Edition, 2016, which is incorporated by reference herein in its entirety.

In some instances, the non-silicone fatty compounds include one or more waxes. The waxes generally have a melting point of from 35-120° C., at atmospheric pressure. Non-limiting examples of waxes in this category include for example, synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, sunflower seed wax (*Helianthus annuus*), acacia decurrents flower wax, or a mixture thereof.

In one embodiment, the composition includes waxes. Mention may be made, among the waxes capable of being used as non-silicone fatty compounds, of animal waxes, such as beeswax; vegetable waxes, such as sunflower seed (*helianthus annuus*), carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis.

In some instance, the non-silicone fatty compounds include one or more non-silicone oils. The term "oil" as used herein describes any material which is substantially insoluble in water. Suitable non-silicone oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Suitable low viscosity oils have a viscosity of 5-100 mPas at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palm itate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isodecanol, polyglyceryl-3-diisostearate, or combinations thereof. The high viscosity oils generally have a viscosity of 200-1,000,000, or 100,000-250,000, mPas at 25° C. Such oils include castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Mineral oils, such as liquid paraffin or liquid petroleum, or animal oils, such as perhydrosqualene or arara oil, or alternatively of vegetable oils, such as sweet almond, calophyllum, palm, castor, avocado, jojoba, olive or cereal germ oil, may be utilized. It is also possible to use esters of these oils, e.g., jojoba esters. Also useful are esters of lanolic acid, of oleic acid, of lauric acid, of stearic acid or of myristic acid; esters of alcohols, such as oleyl alcohol, linoleyl or linolenyl alcohol, isostearyl alcohol or octyldodecanol; and/or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

Silicones

The hair treatment and/or booster compositions of the instant disclosure may optionally include one or more silicones. Nonetheless, as mentioned throughout the instant disclosure, in some instances the compositions are free or essentially free of silicones. In other words, one or more of the following silicones may be optionally included or optionally excluded from the hair treatment and/or booster compositions.

Silicones include, but are not limited to, polyorganosiloxanes, polyalkylsiloxanes, polyarylsiloxanes, polyalkarylsiloxanes, polyestersiloxanes, or mixtures thereof. Non-limiting examples include dimethicone, cyclomethicone (cyclopentasiloxane), amodimethicone, trimethyl silyl amodimethicone, phenyl trimethicone, trimethyl siloxy silicate, polymethylsilsesquioxane or mixtures thereof.

In some instances, the hair treatment and/or booster compositions include (or exclude) one or more silicones selected from the group consisting of polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), non-ionic dimethicone copolyols, dimethicone copolyol esters, dimethicone copolyol quaternium nitrogen containing compounds, dimethicone copolyol phosphate esters, or mixtures thereof.

The hair treatment and/or booster compositions may include (or exclude) one or more silicone oils, for example one or more non-phenyl silicone oils and/or one or more phenyl silicone oils. The silicone oil is preferably apolar. An "apolar silicone oil" is intended to denote a silicon oil that does not comprise any ionic or ionisable group(s), and preferably does not comprise any oxyalkylenated(C2-C4) unit(s) (preferably oxyethylene, oxypropylene), or glycerol unit(s).

Representative examples of non-volatile non-phenyl silicone oils which may be mentioned include polydimethylsiloxanes; alkyl dimethicones; vinylmethyl methicones; and also silicones modified with aliphatic groups and/or with functional groups such as hydroxyl, thiol and/or amine groups. It should be noted that "dimethicone" (INCI name) corresponds to a poly(dimethylsiloxane) (chemical name), which is particularly preferred in some instances.

The non-volatile non-phenyl silicone oil is preferably chosen from non-volatile dimethicone oils. In particular, these oils can be chosen from the following non-volatile oils:

polydimethylsiloxanes (PDMSs);

PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference ABIL WAX 9801 from Evonik Goldschmidt;

PDMSs comprising aliphatic groups, or functional groups such as hydroxyl, thiol and/or amine groups;

polyalkylmethylsiloxanes substituted with functional groups such as hydroxyl, thiol and/or amine groups; and polysiloxanes modified with fatty acids, fatty alcohols or polyoxyalkylenes, or mixtures thereof.

Preferably, non-volatile, non-phenyl silicone oils are chosen from polydimethylsiloxanes, alkyl dimethicones, and also PDMSs comprising aliphatic groups, in particular C2-C24 alkyl groups, and/or functional groups such as hydroxyl, thiol, and/or amine groups.

The non-phenyl silicone oil may be chosen in particular from silicones of the following formula:

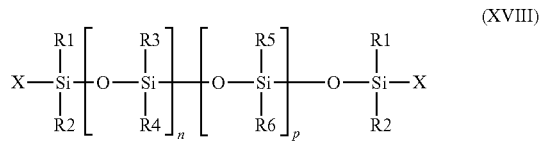
(XVIII)

wherein:
$R_1$, $R_2$, $R_5$, and $R_6$, which may be identical or different, are independently chosen from alkyl radicals containing 1 to 6 carbon atoms,
$R_3$ and $R_4$, which may be identical or different, are independently chosen from alkyl radicals containing from 1 to 6 carbon atoms, a vinyl radical, an amine radical, or a hydroxyl radical,
X is an alkyl radical containing from 1 to 6 carbon atoms, a hydroxyl radical, or an amine radical, and
n and p are integers chosen so as to have a fluid compound, in particular of which the viscosity at 25° C. is between 9 centistokes (cSt) and 800 000 (cSt).

As non-volatile, non-phenyl silicone oils which can be used according to the invention, mention may be made of those for which:
the substituents $R_1$ to $R_6$ and X represent a methyl group, and p and n are such that the viscosity is 500 000 cSt, for example the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning,
the substituents $R_1$ to $R_6$ and X represent a methyl group, and p and n are such that the viscosity is 60 000 cSt, for example the product sold under the name Dow Corning 200 Fluid 60 000 CS by the company Dow Corning, and the product sold under the name Wacker Belsil DM 60 000 by the company Wacker,
the substituents $R_1$ to $R_6$ and X represent a methyl group, and p and n are such that the viscosity is 100 cSt or 350 cSt, for example the products sold respectively under the names Belsil DM100 and Dow Corning 200 Fluid 350 CS by the company Dow Corning,
the substituents $R_1$ to $R_6$ represent a methyl group, the group X represents a hydroxyl group, and n and p are such that the viscosity is 700 cSt, for example the product sold under the name Baysilone Fluid T0.7 by the company Momentive.

Miscellaneous Ingredients

In addition to the above-referenced fatty compounds and silicones, the hair treatment and/or booster compositions of the present disclosure may also optionally comprise additional miscellaneous ingredients or additives such as other conditioning agents, thickening agents, cationic agents, humectants, preservatives, chelating agents, UV filters, pH adjusters, fragrance, pigments/colorants, and anti-dandruff/seborrheic agents. Many conditioning agents are known to those skilled in the art and need not be specifically listed herein. Nonetheless, a non-limiting example of miscellaneous ingredients include other alkyl amines, such as primary, secondary, and tertiary fatty amines, ester oils, and humectants such as glycerin. Alkyl amines include those having one long alkyl chain of preferably from 10 to 30 carbon atoms.

Compositions, Methods of Use and Application, and Kits

The hair treatment and/or booster compositions described throughout the instant disclosure may be in a variety of different forms, for example, gels, lotions, creams, emulsions, pastes, milks, sprays, serums, and the like. The compositions may be rinse-off or leave-in treatments.

In various embodiments, the hair treatment and/or booster compositions may be in the form of an aqueous solution.

In various embodiments, the hair treatment and/or booster compositions may be in the form of a dispersion.

In various embodiments, the hair treatment and/or booster compositions may be in the form of an emulsion, such as an oil-in-water (O/W) emulsion.

In an embodiment, the hair treatment composition is a shampoo, e.g. an aqueous shampoo.

In an embodiment, the hair treatment composition is a conditioner or a masque, e.g. an O/W emulsion.

In an embodiment, the hair treatment composition is a pre-shampoo treatment product.

In an embodiment, the hair treatment composition is a leave-in treatment for conditioning and/or styling and/or shaping hair.

When the hair treatment compositions of the instant disclosure have cleansing and/or conditioning properties, the cleansing compositions may be designated as a "shampoo," a "conditioning shampoo," an "all-in-one conditioning and shampooing composition," a "cream shampoo," a "cream rinse," a "cleansing cream," and variations thereof.

Thus, in certain embodiments, the instant disclosure is directed to methods of treating keratinous substrates such as hair, the method comprising the steps of:
(1) combining a booster composition according to the disclosure with a hair treatment composition according to the disclosure to form a hair care system;
(2) contacting the keratinous substrates with the hair care system; and
(3) optionally, rinsing the keratinous substrates.

Additionally, when used on hair, the hair care systems provide a variety of desirable cosmetic and styling benefits to the hair, for example, smoothness, detangling, and shine. Accordingly, the hair care systems are useful in methods for cleansing hair, methods of conditioning hair, and methods for imparting frizz control, smoothness, detangling, and/or shine to hair. Accordingly, the instant disclosure encompasses methods for treating hair with the hair care systems of the instant disclosure. Such methods may include simply applying a composition or mixture resulting from the combination of the hair treatment compositions and the booster compositions of the instant disclosure to the hair, and optionally rinsing the hair.

In some cases, methods of using the hair care system include shampooing and/or conditioning the hair with the mixture resulting from the combination of the hair treatment compositions and the booster compositions of the instant disclosure. Such methods typically include applying an effective amount of a mixture resulting from the combination of the hair treatment compositions and the booster compositions of the instant disclosure to the hair, allowing the mixture to remain on the hair for a period of time, and subsequently optionally rinsing the mixture from the hair. The period of time for which the mixture is allowed to remain on the hair is usually not long, e.g., not longer than about 5 minutes. Usually, the mixture is merely allowed to remain on the hair for a period of time sufficient to incorporate the mixture throughout the hair, for example, by lathering or spreading the mixture throughout the hair using one's hands. The amount of time is sufficient for the mixture to interact with the hair and any dirt, oil, contamination, etc., that may exist on the hair so that when rinsed, the dirt, oil, contamination, etc., can be effectively removed from the hair and the conditioning agents of the mixture can interact with the hair to condition it. Thus, the mixture may be allowed to remain on the hair for about 5 seconds to about 30 minutes, about 5 seconds to about 15 minutes, about 5 seconds to about 10 minutes, about 5 seconds to about 5 minutes, about 10 seconds to about 5 minutes, or about 10 seconds to about 3 minutes.

As is common when using shampoo and/or conditioner and/or masque compositions, the hair may be wetted or rinsed with water prior to application of the mixture resulting from the combination of the hair treatment and booster compositions of the instant disclosure. Having water already in the hair can be helpful, e.g. for creating lather when applying compositions such as shampoos because the water interacts with the surfactants of the shampoo's surfactant system.

Typically, a shampoo and a conditioner are used in a hair care routine in the form of a bundle system in order to cleanse then condition the hair. Optionally, another composition, e.g. a masque, may be used after a conditioner in order to impart deeper conditioning to the hair or to deliver other active or benefit agents such as styling agent to the hair. Optionally, a pre-shampoo treatment composition may also be applied onto hair before shampooing in order to deliver additional benefits to the hair. Optionally, an in-shower treatment composition may be mixed, in situ on hair or before treating hair, with a shampoo and/or conditioner in order to enhance the cleansing and/or conditioning of the hair. As such, it is possible to have kits comprising one, two, three, or more of these compositions, in addition to the booster composition of the instant disclosure, each composition packaged separately.

In accordance with the instant disclosure, the kit can comprise:
(1) at least one container comprising a booster composition comprising:
 (a) at least one ionic polymer functionalized with at least one carboxylic acid moiety;
 (b) optionally, at least one compound selected from:
  (i) at least one alkoxysilane;
  (ii) at least one nonionic latex polymer; and
  (iii) a mixture thereof;
 (c) at least one thickener; and
 (d) a cosmetically acceptable carrier; and
(2) at least one container comprising a hair treatment composition comprising at least one surfactant selected from at least one anionic surfactant, at least one amphoteric surfactant, at least one cationic surfactant, at least one nonionic surfactant, or mixtures thereof;
where each of the containers of the kit are packaged separately. Any known means of packaging the containers separately in a kit may be used, e.g. separate bottles or containers, a single bottle or container with separate compartments, etc.

Implementation of the present disclosure is provided by way of the following Examples. The Examples serve to illustrate the technology, without being limiting in nature.

EXAMPLES

The following Examples are intended to be non-restrictive and explanatory only. The ingredient amounts in the compositions/formulas described below are expressed in % by weight, based on the total weight of the composition.

Several formulas were produced having the ingredients as listed in the tables below. The balance of all formulas was water.

Where the term "neutralized APTES" appears, a 20% active APTES solution was prepared by using 2.125% phosphoric acid and 3.6% lactic acid (fully neutralized).

Example I: Key Raw Materials or Ingredients

TABLE 1

| Representative Polymers and Actives | |
|---|---|
| Polymer type | Active Ingredient Name and Trade Name |
| Ionic polymer(s) - bimodal agent* amphoteric latex polymer 1 | Polyquaternium-91 (AND) Polyacrylate-15, available in the raw material known by the tradename SYNTRAN PC5500, from Interpolymer |
| Ionic polymer(s) - bimodal agent amphoteric latex polymer 2 | Polyquaternium-91 (AND) Polyacrylate-15, S, available in the raw material known by the tradename SYNTRAN PC5330, from Interpolymer |
| Ionic polymer(s) - bimodal agent amphoteric latex polymer 3 | Polyacrylate-21 (and) Acrylates/Dimethylaminoethyl Methacrylate copolymer, available in the raw material known by the tradename SYNTRAN PC5100-CG, from Interpolymer |
| Ionic polymer(s) - bimodal agent amphoteric latex polymer 4 | Acrylates/ethylhexyl acrylate/hema copolymer (and) acrylates/diethylaminoethyl methacrylate/ethylhexyl acrylate copolymer, available in the raw material known by the tradename SYNTRAN PC5775, from Interpolymer |
| Ionic polymer(s) - bimodal agent amphoteric latex polymer 5 | Polyacrylate-15 (and) polyacrylate-17, available in the raw material known by the tradename SYNTRAN PC5227 CG, from Interpolymer |
| Ionic polymer(s) - amphoteric non-latex polymer 1 | Polyquaternium-22, available in the raw material known by the tradename MERQUAT 280, from Nalco/Lubrizol |

TABLE 1-continued

Representative Polymers and Actives

| Polymer type | Active Ingredient Name and Trade Name |
| --- | --- |
| Ionic polymer(s) - amphoteric non-latex polymer 2 | Polyquaternium-39, available in the raw material known by the tradename MERQUAT 3330PR, from Nalco/Lubrizol |
| Ionic polymer(s) - amphoteric non-latex polymer 3 | Polyquaternium-47, available in the raw material known by the tradename MERQUAT 2001, from Nalco/Lubrizol |
| Ionic polymer(s) - amphoteric non-latex polymer 4 | Polyquaternium-53, available in the raw material known by the tradename MERQUAT 2003PR, from Nalco/Lubrizol |
| Ionic polymer(s) - anionic non-latex polymer 1 | Acrylates/C10-30 Alkyl Acrylate Crosspolymer, available in the raw material known by the tradename PEMULEN TR-1, from Lubrizol |
| Nonionic latex polymer - nonionic acrylates copolymer latex | Acrylates Copolymer, CAS #: 25035-69-2, available in the raw material known by the tradename DAITOSOL 5000 AD, from Daito Kasei Kogyo |
| Organosilicone - alkoxysilane | Aminopropyl triethoxysilane (APTES), available in the raw material known by the tradename XIAMETER OFS-6011 SILANE, from Dow Corning (Dow Chemical) |

*Bimodal agent in the present disclosure may also referred to herein as amphoteric latex polymer(s)

Example II: Booster Formulations

TABLE 2

Booster Formulation 1 (In-Shower Gel 1)

| Component (US INCI NAMES OF INGREDIENTS) | Concentration Wt. % (Active) |
| --- | --- |
| Thickeners (Hydroxypropyl guar, Hydroxyethyl cellulose) | 1.4 |
| Amphoteric non-latex polymer 3 (Polyquaternium-47) | 2.0 |
| Additives - preservatives, fragrance, pH adjusters, etc. | <2.0 |
| Water | q.s. to 100 |

TABLE 3

Booster Formulation 2 (In-Shower Gel 2)

| Component (US INCI NAMES OF INGREDIENTS) | Concentration Wt. % (Active) |
| --- | --- |
| Thickeners (Hydroxypropyl guar, Hydroxyethyl cellulose) | 1.4 |
| Amphoteric non-latex polymer 3 (Polyquaternium-47) | 2.0 |
| Alkoxysilane (Aminopropyl triethoxysilane (APTES)) | 0.5 |
| Additives - preservatives, fragrance, pH adjusters, etc. | <2.0 |
| Water | q.s. to 100 |

TABLE 4

Booster Formulation 3 (In-Shower Gel 3)

| Component (US INCI NAMES OF INGREDIENTS) | Concentration Wt. % (Active) |
| --- | --- |
| Thickeners (Hydroxypropyl guar, Hydroxyethyl cellulose) | 1.6 |
| Nonionic Surfactants (ceteareth-27, laureth 21, Poloxamer 235) | 0.3 |
| Cationic Surfactant (cetrimonium chloride) | 0.5 |
| Silicones (cyclohexasiloxane) | 0.4 |
| Fatty compounds - Plant oils (*Elaeis Guineensis* (Palm) Oil) | 0.5 |
| Ionic polymer - Bimodal agent: Amphoteric Latex Polymer 2 (Polyquaternium-91 (and) Polyacrylate-15) | 1.5 |
| Alkoxysilane (Aminopropyl triethoxysilane (APTES)) | 0.5 |
| Nonionic Latex Polymer - nonionic acrylates copolymer latex (Acrylates Copolymer) | 0.5 |
| Water-Soluble Organic Solvent(s) | 0.1 |
| Additives - preservatives, fragrance, pH adjusters, vitamins, etc. | <2.0 |
| Water | q.s. to 100 |

Example III: Hair Testing

Booster formulations 1-3 (in-shower gels 1-3) were tested on hair according to the following procedure. Two-gram hair swatches (natural frizzy hair from HIP) were treated with either (i) a commercial shampoo (0.4 g shampoo/g hair) (control) or (ii) a shampoo composition resulting from the combination of the commercial shampoo (0.4 g shampoo/g hair) combined with one of booster formulations 1-3 (0.2 g formulation/g hair) for 30 seconds. The treated hair was then rinsed with water (35° C.±5° C.) for 30 seconds. Next, the hair was then further massaged with either (iii) a commercial conditioner (0.4 g conditioner/g hair) (control) or with (iv) a conditioner composition resulting from the combination of the commercial conditioner (0.4 g conditioner/g hair) with one of booster formulations 1-3 (0.2 g formulation/g hair) for 30 seconds. The treated hair was then rinsed with water (35° C.±5° C.) for 30 seconds. The conditioner can also sit on hair for 30 seconds prior to rinsing. After excess water was squeezed out, the treated hair swatches were allowed to stand at ambient conditions overnight.

Thus, the designated hair swatches were treated with a shampoo/conditioner bundle system or hair care routine in which either the shampoo or the conditioner or both were first combined or mixed with a booster formulation according to the disclosure, and the resulting mixture was applied onto hair.

The degree of frizz of the hair on the swatches was assessed before and after the hair swatches were placed in a humidity chamber (80% RH, 25° C.) for 4-8 hours. Hair frizziness was assessed by rating the degree of frizziness from 1-5 (with 5 being the frizziest).

Example III-A: Hair Treated with Shampoo and/or Conditioner Containing an Amphoteric Non-Latex Polymer Following the above procedure, the hair was treated and assessed for frizz:

| Treatment | Before High Humidity | After High Humidity |
|---|---|---|
| Commercial Shampoo + Commercial Conditioner (control bundle system) | 3 | 4 |
| Commercial Shampoo mixed with in-shower gel 1 + Commercial Conditioner | 1 | 3 |
| Commercial Shampoo + Commercial Conditioner mixed with in-shower gel 1 | 2.5 | 3.5 |
| Commercial Shampoo mixed with in-shower gel 1 + Commercial Conditioner mixed with in-shower gel 1 | 1.5 | 2 |

Hair treated with a shampoo and/or conditioner mixed with the in-shower gel booster composition showed better frizz control at ambient and high humidity conditions than the hair treated with the control bundle system. At ambient conditions, the hair treated with a shampoo mixed with the in-shower gel booster composition followed by a commercial conditioner exhibited the least amount of frizz compared to the hair subjected to the other treatments.

The observed anti-frizz property was long-lasting at high humidity as well, i.e., while the degree of frizz increased in all test hair swatches, the degree of frizz in the hair treated with a shampoo and/or conditioner mixed with the in-shower gel booster composition was still significantly less than that of the hair treated with the control bundle system. At high humidity conditions, the hair treated with a shampoo mixed with the in-shower gel booster composition followed by a conditioner mixed with the in-shower gel booster composition exhibited the least degree of frizz compared to the hair subjected to the other treatments, and the least increase in degree of frizziness from ambient to high humidity conditions.

Example III-B: Hair Treated with Shampoo and/or Conditioner Containing an Amphoteric Non-Latex Polymer and APTES Following the above procedure, the hair was treated and assessed for frizz:

| Treatment | Before High Humidity | After High Humidity |
|---|---|---|
| Commercial Shampoo + Commercial Conditioner (control bundle system) | 4 | 5 |
| Commercial Shampoo mixed with in-shower gel 2 + Commercial Conditioner | 1 | 2 |
| Commercial Shampoo + Commercial Conditioner mixed with in-shower gel 2 | 3.5 | 3.5 |
| Commercial Shampoo mixed with in-shower gel 2 + Commercial Conditioner mixed with in-shower gel 2 | 3 | 3 |

Hair treated with a shampoo and/or conditioner mixed with the in-shower gel booster composition showed better frizz control at ambient and high humidity conditions than the hair treated with the control bundle system. At ambient conditions, the hair treated with a shampoo mixed with the in-shower gel booster composition followed by a commercial conditioner exhibited the least amount of frizz compared to the hair subjected to the other treatments.

The observed anti-frizz property was long-lasting at high humidity as well, i.e., the degree of frizz in the hair treated with a shampoo and/or conditioner mixed with the in-shower gel booster composition was still significantly less than that of the hair treated with the control bundle system. Moreover, from ambient to high humidity conditions, the hair treated with a shampoo mixed with the in-shower gel booster composition and/or with a conditioner mixed with the in-shower gel booster composition exhibited the same or only a small increase in the degree of frizz, which was still significantly less than the degree of frizz in the hair subjected to the control bundle system.

Example III-C: Hair Treated with Shampoo and/or Conditioner Containing an Amphoteric Latex Polymer and APTES Following the above procedure, the hair was treated and assessed for frizz:

| Treatment | Before High Humidity | After High Humidity |
|---|---|---|
| Commercial Shampoo + Commercial Conditioner (control bundle system) | 5 | 5 |
| Commercial Shampoo mixed with in-shower gel 3 + Commercial Conditioner | 2 | 2 |
| Commercial Shampoo + Commercial Conditioner mixed with in-shower gel 3 | 2 | 2 |

Hair treated with a shampoo or conditioner mixed with the in-shower gel booster composition showed better frizz control at ambient and high humidity conditions than the hair treated with the control bundle system.

The observed anti-frizz property was long-lasting at high humidity as well, i.e., the degree of frizz in the hair treated with a shampoo or conditioner mixed with the in-shower gel booster composition was still significantly less than that of the hair treated with the control bundle system. In fact, from ambient to high humidity conditions, the hair treated with a shampoo mixed with the in-shower gel booster composition or with a conditioner mixed with the in-shower gel booster composition exhibited the same degree of frizz, which was very much less than the degree of frizz in the hair subjected to the control bundle system.

In summary, from the frizz assessments above, at ambient conditions, the degree of frizz in hair treated with a shampoo and/or conditioner mixed with the hair treatment or in-shower gel booster compositions of the invention was surprisingly found to be always less than the degree of frizz in hair treated with the control bundle systems. More surprisingly, even if the degree of frizz increased in certain treatments at high humidity for the hair treated in accordance with the invention, the degree of frizz in such hair was still significantly less than that observed for the hair treated with the control bundle systems.

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "hair care system" and variations thereof, and "hair care mixture" and variations thereof, are used interchangeably to denote a combination or mixture of (1) a booster composition containing at least one ionic polymer functionalized with at least one carboxylic acid moiety; optionally, at least one compound selected from an alkoxysilane, a nonionic latex polymer, or mixtures thereof; a thickening agent; and a cosmetically acceptable carrier; and (2) a hair treatment composition containing at least one surfactant selected from anionic surfactants, amphoteric surfactants, cationic surfactants, nonionic surfactants, or mixtures thereof.

It is to be understood that, unless otherwise specified, steps of any method described herein may be performed in any order.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions can be modified in all instances by the term "about," meaning within +/−1%, 2%, 3%, 4%, or 5% of the indicated number.

Some of the various categories of components identified for the hair-treatment compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

All numbers herein are understood to be modified by "about," whether or not expressly stated. Additionally, all numbers are intended to represent exact figures as additional embodiments, whether or not modified by "about." For example, "an amount of about 1%" includes an amount of exactly 1%. As a further example, "an amount of about 1%" includes an amount of about 1%. The term "about" is generally understood to encompass a range of +/−10% from the stated number, and is intended to cover amounts of +/−1%, 2%, 3%, 4%, 5%, 6%, 7%, 8%, 9%, and 10%.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 1% by weight of a specific material added to a composition, based on the total weight of the compositions (provided that an amount of less than 1% by weight does not materially affect the basic and novel characteristics of the claimed invention. Similarly, the compositions may include less than 0.5 wt %, less than 0.1 wt %, less than 0.05 wt %, or less than 0.01 wt %, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair shampooing or conditioning system comprising a mixture of:
   (1) a booster composition comprising:
      (a) an ionic polymer component comprising at least one ionic polymer functionalized with at least one carboxylic acid moiety chosen from bimodal agents comprising a polymeric component having at least one anionic functionality and a polymeric component having at least one cationic functionality;
      (b) optionally, at least one compound selected from:
         (i) at least one alkoxysilane;
         (ii) at least one nonionic latex polymer; or
         (iii) mixtures of two or more thereof;
      (c) at least one thickening agent; and
      (d) a cosmetically acceptable carrier; and
   (2) at least one hair treatment composition comprising at least one surfactant selected from anionic surfactants, amphoteric surfactants, cationic surfactants, nonionic surfactants, or mixtures of two or more thereof.

2. The hair shampooing or conditioning system of claim 1, wherein the total amount of ionic polymers functionalized with at least one carboxylic acid moiety in the booster composition ranges from about 0.1 wt % to about 10 wt % of the total booster composition, wherein the at least one ionic polymer includes at least one unsaturated alkylene-containing-carboxylic acid-based monomer, or wherein the at least one ionic polymer includes at least one (meth)acrylic acid-based and/or at least one (meth)acrylate-based monomer.

3. The hair shampooing or conditioning system of claim 1, wherein the at least one bimodal agent is selected from i) polyquaternium-91 (and) polyacrylate-15, ii) polyacrylate-21 (and) acrylates/dimethylaminoethyl methacrylate copolymer, iii) acrylates/ethylhexyl acrylate/hema copolymer (and) acrylates/diethylaminoethyl methacrylate/ethylhexyl acrylate copolymer, iv) polyacrylate-15 (and) polyacrylate-17, v) polyacrylate-18 (and) polyacrylate-19, vi) polyacrylate-16, or mixtures of two or more thereof.

4. The hair shampooing or conditioning system of claim 1, wherein the ionic polymer component (a) further comprises at least one amphoteric polymer selected from polyquaternium-22, polyquaternium-39, polyquaternium-47, polyquaternium-53, polyquaternium-61, polyquaternium-69, polyquaternium-86, polyquaternium-95, or mixtures of two or more thereof.

5. The hair shampooing or conditioning s stem of claim 1, wherein the ionic polymer component (a) further comprises at least one anionic polymer selected from polyacrylate-15, polyacrylate-21, polyacrylate-17, polyacrylate-18, polyacrylate-19, a branched anionic acrylate copolymer polyacrylate-2 crosspolymer, acrylates crosspolymer-3, polyacrylate-14, latex acrylates copolymer, styrene/acrylates/ammonium methacrylate copolymer, ammonium acrylates copolymer, polyurethane-1, polyurethane-34, polyurethane-14/AMP-acrylates copolymer, acrylates copolymers of two or more monomers of (meth)acrylic acid, simple esters of acrylates copolymers of two or more monomers of (meth) acrylic acid, acrylic acid/ethyl acrylate/N-tert-butylacrylamide terpolymers, vinyl acetate/vinyl tert-butylbenzoate/crotonic acid terpolymers, crotonic acid/vinyl acetate/vinyl neododecanoate terpolymers, methyl vinyl ether/monoesterified maleic anhydride copolymers, copolymers of methacrylic acid and of methyl methacrylate, copolymers of methacrylic acid and of ethyl acrylate, vinyl acetate/crotonic acid copolymers, vinyl acetate/crotonic acid copolymers grafted by polyethylene glycol, branched block anionic polymer, acrylates crosspolymer-4 acrylates copolymer, carbomers, acrylates/C10-30 alkyl acrylates crosspolymers, acrylates/steareth-20 methacrylate crosspolymer, acrylates/palmeth-25 acrylate copolymer, acrylates/palmeth-20 acrylate copolymer, octylacrylamide/acrylates/butylamino ethyl (meth)acrylate copolymer, acrylic acid/C10-C30 alkyl acrylate crosslinked copolymers, crotonic acid/vinyl acetate/vinyl neododecanoate terpolymers, acrylates copolymer, polyacrylate-2, polyacrylate-21, oxyalkylenated stearyl methacrylate/ethylacrylate/methacrylic acid terpolymer, methacrylic acid/ethyl acrylate/oxyethylenated stearyl methacrylate copolymer (55/35/10); (meth)acrylic acid/ethyl acrylate/25 EO oxyethylenated behenyl methacrylate copolymer, methacrylic acid/ethyl acrylate/steareth-10 allyl ether crosslinked copolymer, an alpha olefin hydrocarbon-maleic anhydride copolymer wax, or mixtures of two or more thereof.

6. The hair shampooing or conditioning system of claim 1, wherein the ionic polymer component (a) further comprises at least one cationic polymer selected from polyquaternium-91, polyquaternium-4, polyquaternium-11, polyquaternium-16, polyquaternium-68, or mixtures of two or more thereof.

7. The hair shampooing or conditioning system of claim 1, wherein the total amount of compound (b) ranges from about 0.05 wt % to about 10 wt % of the total booster composition.

8. The hair shampooing or conditioning system of claim 1, comprising at least one alkoxysilane having at least one solubilizing functional group and at least one amino substituent.

9. The hair shampooing or conditioning system of claim 1, comprising at least one nonionic latex polymer selected from acrylates copolymer, polyacrylate-2 crosspolymer, styrene/acrylates copolymer, acrylates/ethylhexyl acrylate copolymer, or mixtures of two or more thereof.

10. The hair shampooing or conditioning system of claim 1, wherein the booster composition comprises at least one thickening agent chosen from polysaccharides.

11. The hair shampooing or conditioning system of claim 1, wherein in the at least one hair treatment composition:
the at least one anionic surfactant is selected from alkyl sulfates, alkyl ether sulfates, acyl isethionates, acyl sarcosinates, alkyl sulfonates, alkyl sulfosuccinates, alkyl sulfoacetates, acyl amino acid surfactants other than acyl sarcosinates and selected from acyl taurates, acyl glycinates, acyl glutamates, alkoxylated monoacids, salts thereof, or mixtures of two or more thereof;
the at least one amphoteric surfactant is selected from betaines, alkyl amphoacetates, alkyl amphoproprionates, salts thereof, or mixtures of two or more thereof;
the at least one cationic surfactant is selected from a quaternary ammonium compound that is a mono or double chain quaternary ammonium compound, wherein each chain independently has from about 14 to about 30 carbon atoms; and the quaternary ammonium compound has a cosmetically acceptable counterion selected from chloride, bromide, methosulfate, or mixtures of two or more thereof; and/or
the at least one nonionic surfactant is selected from alkyl polyglucosides, fatty alcohols, alkoxylated fatty alcohols, sorbitan derivatives, glyceryl esters, or mixtures of two or more thereof.

12. The hair shampooing or conditioning system of claim 1, wherein the at least one hair treatment composition is: (i) a shampoo containing at least one anionic surfactant, and optionally, at least one amphoteric surfactant; or (ii) a conditioner or masque containing at least one cationic surfactant; or (iii) a pre-shampoo treatment product or a leave-in treatment product or an in-shower treatment product containing at least one nonionic surfactant and/or at least one cationic surfactant.

13. A method of treating hair, comprising:
(A) combining the booster composition of claim 1 with the at least one hair treatment composition of claim 1, wherein the hair treatment composition is selected from:
(i) a first hair treatment composition comprising a shampoo containing the at least one anionic surfactant, and optionally, the at least one amphoteric surfactants in order to form a shampoo mixture; and/or
(ii) a second hair treatment composition comprising a conditioner or a masque containing the at least one cationic surfactant in order to form a conditioner mixture or a masque mixture; and/or
(iii) a third hair treatment composition comprising a pre-shampoo treatment product or an in-shower treatment product or a leave-in treatment product containing the at least one cationic surfactant and/or the at least one nonionic surfactant in order to form a pre-shampoo treatment mixture or a leave-in treatment mixture; and (B) contacting hair with the shampoo mixture or the conditioner mixture or the masque mixture or the pre-shampoo treatment mixture or the leave-in treatment mixture;
wherein the booster composition is separately combined with one or more of the first, the second, and the third hair treatment compositions.

14. A method of treating hair with the hair shampooing or conditioning system of claim 1, wherein the method comprises (i) contacting hair with the booster composition; and (ii) contacting the hair with the at least one hair treatment composition; wherein either (i) or (ii) is the first step.

15. A method for treating hair with a hair shampooing or conditioning system, the method comprising the steps of:
(A) combining, to form the hair shampooing or conditioning system:
(1) a booster composition comprising:
(a) an ionic polymer component comprising at least one ionic polymer functionalized with at least one carboxylic acid moiety chosen from bimodal agents comprising a polymeric component having at least one anionic functionality and a polymeric component having at least one cationic functionality;
(b) optionally, at least one compound selected from:
(i) at least one alkoxysilane;
(ii) at least one nonionic latex polymer; or
(iii) mixtures of two or more thereof;
(c) at least one thickening agent; and
(d) a cosmetically acceptable carrier; and
(2) at least one hair treatment composition comprising at least one surfactant selected from anionic surfactants, amphoteric surfactants, cationic surfactants, nonionic surfactants, or mixtures of two or more thereof;
(B) contacting the hair with the hair shampooing or conditioning system; and
(C) optionally, rinsing the hair;
wherein the at least one hair treatment composition is selected from:
(i) a first hair treatment composition comprising a shampoo containing at least one anionic surfactant, and optionally at least one amphoteric surfactants;
(ii) a second hair treatment composition comprising a conditioner or a masque containing at least one cationic surfactant; and
(iii) a third hair treatment composition comprising a pre-shampoo treatment product or leave-in treatment product containing at least one cationic surfactant and/or at least one nonionic surfactant.

16. The method of claim 15, comprising combining the booster composition, separately, with one or more of the first hair treatment composition and/or the second hair treatment composition and/or the third hair treatment composition in a weight ratio of booster composition to hair treatment composition ranging from about 0.2:1 to about 5:1.

17. The method of claim 15, the method comprising treating hair according to a layer by layer method by the steps: (I) contacting hair with the booster composition; and (II) contacting the hair with the at least one hair treatment composition; wherein either (I) or (II) is the first step.

18. A multicomponent kit comprising:
(1) a booster composition comprising:
(a) an ionic polymer component comprising at least one ionic polymer functionalized with at least one carboxylic acid moiety chosen from bimodal agent(s) comprising a polymeric component having at least one anionic functionality and a polymeric component having at least one cationic functionality;
(b) optionally, at least one compound selected from:
(i) at least one alkoxysilane;
(ii) at least one nonionic latex polymer; or
(iii) mixtures of two or more thereof;
(c) at least one thickening agent; and
(d) a cosmetically acceptable carrier; and
(2) at least one hair treatment composition comprising at least one surfactant selected from anionic surfactants, amphoteric surfactants, cationic surfactants, nonionic surfactants, or mixtures of two or more thereof,
wherein the hair treatment composition is a shampoo, a conditioner, a masque, a pre-shampoo treatment product, or leave-in treatment product.

* * * * *